US011648263B2

(12) United States Patent
Kennedy

(10) Patent No.: US 11,648,263 B2
(45) Date of Patent: May 16, 2023

(54) MINERAL CATION COMPLEX COMPOSITIONS, FORMULATIONS THEREOF, AND METHODS OF USE THEREOF

(71) Applicant: Lyme Revive Foundation, Austin, TX (US)

(72) Inventor: John Wayne Kennedy, Austin, TX (US)

(73) Assignee: Lyme Revive Foundation, Austin, TX (US)

( * ) Notice: Subject to any disclaimer, the term of this patent is extended or adjusted under 35 U.S.C. 154(b) by 0 days.

(21) Appl. No.: 17/466,974

(22) Filed: Sep. 3, 2021

(65) Prior Publication Data

US 2022/0072037 A1 Mar. 10, 2022

Related U.S. Application Data

(60) Provisional application No. 63/074,982, filed on Sep. 4, 2020.

(51) Int. Cl.
| *A61K 33/34* | (2006.01) |
| *A61K 33/30* | (2006.01) |
| *A61K 33/02* | (2006.01) |
| *A61K 33/04* | (2006.01) |
| *A61K 33/06* | (2006.01) |
| *A61K 45/06* | (2006.01) |

(52) U.S. Cl.
CPC .............. *A61K 33/34* (2013.01); *A61K 33/02* (2013.01); *A61K 33/04* (2013.01); *A61K 33/06* (2013.01); *A61K 33/30* (2013.01); *A61K 45/06* (2013.01)

(58) Field of Classification Search
None
See application file for complete search history.

(56) References Cited

U.S. PATENT DOCUMENTS

| 4,438,083 | A | 3/1984 | Willems et al. |
| 5,679,342 | A | 10/1997 | Houghton et al. |
| 5,968,755 | A | 10/1999 | Roederer et al. |
| 7,163,709 | B2 | 1/2007 | Cook et al. |
| 9,266,785 | B2 | 2/2016 | Kennedy |
| 2003/0118705 | A1 | 6/2003 | Cook et al. |
| 2007/0128295 | A1 | 6/2007 | Kennedy |
| 2011/0129545 | A1 | 6/2011 | Miele |
| 2011/0176988 | A1 | 7/2011 | Okamura et al. |
| 2012/0171130 | A1 | 7/2012 | Kennedy |
| 2014/0212508 | A1 | 7/2014 | Kennedy |
| 2014/0342915 | A1 | 11/2014 | Kennedy |
| 2015/0175432 | A1 | 6/2015 | Gao et al. |
| 2016/0168039 | A1 | 6/2016 | Kennedy |
| 2017/0217846 | A1 | 8/2017 | Kennedy |

FOREIGN PATENT DOCUMENTS

| AU | 2002361658 A1 | 7/2003 |
| AU | 2008318817 A1 | 5/2009 |
| AU | 2012227281 A1 | 10/2012 |
| AU | 2015200841 A1 | 3/2015 |
| AU | 2016259438 A1 | 12/2016 |
| CL | 2015003486 A1 | 11/2016 |
| EP | 2214685 A1 | 8/2010 |
| GB | 2467084 A | 7/2010 |
| RU | 2010122226 A | 12/2011 |
| RU | 2014153697 A | 7/2016 |
| WO | WO2003053170 A1 | 7/2003 |
| WO | WO2009/058857 | 5/2009 |
| WO | WO2014194072 A2 | 12/2014 |
| WO | WO2018/106844 A1 | 6/2018 |

OTHER PUBLICATIONS

Antifungal Disinfectant Activity by Fungicide Challenge—Aspergillus Brasiliensis, Aug. 3, 2020, 2 pages, retrieved Feb. 23, 2022 from https://web.archive.org/web/*/https://zcm25.com/resources/.
Antimicrobial—Bacterial & Fungal Challenge Test 1 4 Lots of Ion Gel ZCM-25, Aug. 30, 2019, 7 pages, retrieved Feb. 23, 2022 from https://web.archive.org/web/*/https://zcm25.com/resources/.
Antimicrobial—Bacterial & Fungal Challenge Test 2—Six Month Stability 3 Lots of Ion Gel ZCM-25, Apr. 2, 2020, 6 pages, retrieved Feb. 23, 2022 from https://web.archive.org/web/*/https://zcm25.com/resources/.
Antimicrobial—Gram Negative—Gram Positive Bacterial Challenge Test of Ion Gel ZCM-25, Dec. 9, 2019, 3 pages, retrieved Feb. 23, 2022 from https://web.archive.org/web/*/https://zcm25.com/resources/.
Antimicrobial—Gram Negative—Gram Positive Bacterial Challenge Test of Ion-ZCM1, Dec. 9, 2019, 3 pages, retrieved Feb. 23, 2022 from https://web.archive.org/web/*/https://zcm25.com/resources/.
Anti-MRSA disinfectant Activity by a Bacterial Challenge MRSA, Aug. 5, 2020, 2 pages, retrieved Feb. 23, 2022 from https://web.archive.org/web/*/https://zcm25.com/resources/.
Antiviral Activity of Ion Gel ZCM-25 on SARS-CoV-2 Equine Viral Arteritis—ZCM-25, Jun. 7, 2020, 13 pages, retrieved Feb. 23, 2022 from https://web.archive.org/web/*/https://zcm25.com/resources/.
Cameron et al., "Evidence Assessments and Guideline Recommendations in Lyme Disease: the Clinical Management of Known Tick Bites, Erythema Migrans Rashes and Persistent Disease," Expert Review of Anti-infective Therapy, vol. 12, Issue 9, 33, pp. 2014.

(Continued)

*Primary Examiner* — Robert T. Crow
*Assistant Examiner* — John P Nguyen
(74) *Attorney, Agent, or Firm* — Cooley LLP

(57) ABSTRACT

The disclosure provides compositions and formulations for the treatment and mitigation disease as well as the restoration of cells to a state of metabolic homeostasis. The disclosure further provides exemplary methods of administering a therapeutically effective amount of a composition or formulation comprising a mineral cation complex and ionic salt to a subject for the treatment of disease or disorder. The disclosure further provides exemplary methods of administering a therapeutically effective amount of a composition or formulation comprising a mineral cation complex and ionic salt to a subject for the maintenance or restoration of cellular metabolic homeostasis.

9 Claims, No Drawings

(56) References Cited

OTHER PUBLICATIONS

Choo et al., "Isolation of a cDNA clone derived from a blood-borne non-A, non-B viral hepatitis genome," Science 244:359-362 (1989).
Cofepris Approval of the Ion Gel ZCM-25, Feb. 2, 2021, 3 pages, retrieved Feb. 23, 2022 from https://web.archive.org/web/*/https://zcm25.com/resources/.
Dermal Irritability 3 Day Dosing Study of Ion Gel ZCM-25 on New Zealand Male Rabbits.—ZCM-25, Jul. 19, 2018, 9 pages, retrieved Feb. 23, 2022 from https://web.archive.org/web/*/https://zcm25.com/resources/.
Dermal Irritability Single High Dose Study of Ion Gel ZCM-25 on New Zealand Male Rabbits—ZCM-25, Aug. 13, 2019, 15 pages, retrieved Feb. 23, 2022 from https://web.archive.org/web/*/https://zcm25.com/resources/.
Interactive Nutrition Facts Label, Vitamins and Minerals Chart 1, U.S. Food & Drug Administration, Mar. 2020, 8 pages.
International Search Report and Written Opinion issued by the International Searching Authority for Application No. PCT/us2021/049152, dated Dec. 16, 2021, 13 pages.
Invitro Toxicity Study of ION-ZCM1 on Human Cells Using an MTT Cytotoxicity Test Method—ZCM-25, 55 pages, Jun. 26, 2018, retrieved Feb. 23, 2022 from https://web.archive.org/web/*/https://zcm25.com/resources/.
Ion Gel ZCM-25 Dosing Comparison Chart—ZCM-25, Jul. 24, 2020, 1 page, retrieved Feb. 23, 2022 from https://web.archive.org/web/*/https://zcm25.com/resources/.
Ion Gel ZCM-25 Phase 1 Clinical Study on Humans—ZCM-25, Oct. 5, 2020, 3 pages, retrieved Feb. 23, 2022 from https://web.archive.org/web/*/https://zcm25.com/resources/.
Ion Gel ZCM-25 User Manual—ZCM-25, Use Case Studies, Sep. 21, 2020, 4 pages, retrieved Feb. 23, 2022 from https://web.archive.org/web/*/https://zcm25.com/resources/.
Ion-ZC1 Antimicrobial Study 1—Bacterial—Fungal—12 Hospital Acquired Pathogens-ACM-25, Jul. 19, 2017, 32 pages, retrieved Feb. 23, 2022 from https://web.archive.org/web/*/https://zcm25.com/resources/.
Ion-ZC1 Antimicrobial Study 2 MRSA Non-biofilm Comparing Vancomycin as a Control—ZCM-25, Mar. 1, 2018, 31 pages, retrieved Feb. 23, 2022 from https://web.archive.org/web/*/https://zcm25.com/resources/.
Ion-ZC1 Antimicrobial Study 3—MRSA in Biofilm—ZCM-25, Mar. 7, 2018, 32 pages, retrieved Feb. 23, 2022 from https://web.archive.org/web/*/https://zcm25.com/resources/.
Ion-ZCM1 is Classified as a Small Molecule—ZCM-25, Mar. 14, 2019, 3 pages, retrieved Feb. 23, 2022 from https://web.archive.org/web/*/https://zcm25.com/resources/.
Iwarson, "The natural course of chronic hepatitis C," FEMS Microbial. Rev. 14:201-204 (1994).
O'Dell, Mineral Interactions Relevant to Nutrient Requirements, J Nutrition 119(12):1832-1838 (1989).
Oxygen Radical Absorbance Capacity—ORAC Activity of ION-ZCM1—ZCM-25, Aug. 16, 2018, 42 pages, retrieved Feb. 23, 2022 from https://web.archive.org/web/*/https://zcm25.com/resources/.
Purcell, "Hepatitis C Virus: Historical Perspective and Current Concepts," FEMS MicrobioL Rev., 14:181-192 (1994).
Research Manual for Ion Gel ZCM-25—ZCM-25, 29 pages, Jul. 20, 2020, retrieved Feb. 23, 2022 from https://web.archive.org/web/*/https://zcm25.com/resources/.
Saito et al., "Hepatitis C virus infection is associated with the development of hepatocellular carcinoma," Proc. Natl. Acad. Sci. USA, 87:6547-6549 (1990).
Tickborne Diseases of the United States, A Reference Manual for Health Care Providers, U.S. Dept. of Health and Human Services, Centers for Disease Control and Prevention, Fourth Edition, 2017, 21 pages.
Wormser et al., "The Clinical Assessment Treatment, and Prevention of Lyme Disease, Human Granulocytic Anaplasmosis, and Babesiosis: Clinical Practice Guidelines by the Infectious Diseases Society of America," Clinical Infectious Diseases, vol. 43, Issue 9, pp. 1089-1134, Nov. 2006.

MINERAL CATION COMPLEX COMPOSITIONS, FORMULATIONS THEREOF, AND METHODS OF USE THEREOF

CROSS-REFERENCE TO RELATED APPLICATIONS

This application claims priority under 35 U.S.C. § 119 to Provisional Patent Application Ser. No. 63/074,982 filed Sep. 4, 2020, herein incorporated by reference in its entirety.

FIELD OF THE INVENTION

The disclosure generally relates to compositions and formulations for use in treating and mitigating disease as well as restoring or maintaining metabolic homeostasis of healthy cells.

BACKGROUND

The following description includes information that may be useful in understanding the present invention. It is not an admission that any of the information provided herein is prior art or relevant to the presently claimed inventions, or that any publication specifically or implicitly referenced is prior art.

The prevalence of disease remains a problem in society today. Alternatively, or in addition, a loss of cellular metabolic homeostasis remains a problem in society today. Organisms constantly face exposure to, and fall victim to, numerous pathogenic agents which can result in physiological consequence, physical impairment, or even death. There is a long-felt yet unmet need in the art for safe and effective compositions and formulations that can treat disease as well as maintain health. The disclosure provides solutions for these unmet needs.

SUMMARY

The following embodiments and aspects thereof are described in conjunction with systems, tools and methods which are meant to be exemplary, not limiting in scope.

In various embodiments, one or more of the above-described problems have been reduced or eliminated, while other embodiments are directed to other improvements.

The disclosure provides a composition comprising: a hexa-aqua moiety comprising six water molecules, one or more cationic mineral(s), and one or more ionic salt(s); wherein the one or more cationic mineral(s) form six coordinate bonds with water ligands to form a hexa-aqua complex.

In some embodiments of the compositions of the disclosure, the one or more cationic minerals comprise chromium, cobalt, copper, gold, iron, manganese, magnesium, molybdenum, nickel, platinum, silver, vanadium, and zinc.

In some embodiments of the compositions of the disclosure, the one or more ionic salts comprise nitrogen, phosphorous, potassium, sulfur, and hydrogen.

In some embodiments of the compositions of the disclosure, the composition further comprises a pharmaceutically acceptable carrier.

In some embodiments of the compositions of the disclosure, the composition further comprises one or more botanical agent(s). In some embodiments, the one or more biological agent(s) comprises Graviola (*Annona muricate*), Bitter Melon (*Momordica charantia*), Esplanheira Santa (*Maytenus illcifolia*), Mullaca (*Physolis angulate*), Vasourinho (*Scoparia dulcis*), Mutamba (*Guazuma ulmifola*), Suma (*Pfaffia paniculata*), Cat's Claw (*Uncaria tomantosa*) and Blood Root (*Sanguinaria canadensis*). In some embodiments, the one or more biological agent(s) comprises *Annona muricate, Momordica charantia, Maytenus illcifolia, Physolis angulate, Scoparia dulcis, Guazuma ulmifola, Pfaffia paniculata, Uncaria tomantosa* and *Sanguinaria canadensis*.

The disclosure provides a formulation comprising a composition of the disclosure, wherein the formulation is suitable for administration in a droplet form, an aerosol form, a vaporized form or a nebulized form.

The disclosure provides a formulation comprising a composition of the disclosure, wherein the formulation is suitable for administration in a liquid form, a suspension form or a rehydrated form.

The disclosure provides a formulation comprising a composition of the disclosure, wherein the formulation is suitable for administration in a semi-solid form.

The disclosure provides a formulation comprising a composition of the disclosure, wherein the formulation is suitable for administration in a solid form, a pill form, a tablet form or a capsule form.

In some embodiments of the formulations of the disclosure, the formulation comprises one or more of an excipient, a filler, a viscosity adjusting agent, a tonicity adjusting agent, a pH adjusting agent, a buffering agent, a purging agent, a co-solvent agent, a preservative agent, a suspension agent, a surfactant agent, a filler agent, a bulking agent, a solvent agent, and a humectant agent. In some embodiments, the tonicity adjusting agent comprises sodium chloride or dextrose. In some embodiments, the pH adjusting agent comprises sodium hydroxide, hydrochloric acid or sulphuric acid. In some embodiments, the buffering agent comprises sodium citrate, sodium phosphate or citric acid. In some embodiments, the purging agent comprises nitrogen. In some embodiments, the co-solvent agent comprises alcohol, polyethylene glycol (PEG) 400 or propylene glycol. In some embodiments, the preservative agent comprises benzalkonium chloride, ethanol, propylene glycol, beczoyl alcohol, chlorobutanol or methyl paraben. In some embodiments, the suspension agent comprises carboxymethylcellulose (CMC) or sodium CMC. In some embodiments, the surfactant agent comprises poractant, poracant alfa, polysorbate 80 or polysorbate 20. In some embodiments, the humectant agent comprises glycerin.

In some embodiments of the formulations of the disclosure, a droplet form comprises a droplet size of between 0.5 µm and 7.0 µm, inclusive of the endpoints.

In some embodiments of the formulations of the disclosure, composition is suitable for administration by a nebulizer. In some embodiments, the nebulizer comprises a nozzle array and an aqueous chamber. In some embodiments, the nozzle array comprises an air jet nebulizer, an electronic nebulizer, an ultrasonic nebulizer, a vibrating mesh nebulizer, a vibrating membrane nebulizer, a vibrating plate nebulizer, or a vibration generator.

The disclosure provides a device comprising a composition of the disclosure.

The disclosure provides a device comprising a formulation of the disclosure.

In some embodiments of the devices of the disclosure, including those devices comprising a composition or a formulation of the disclosure, the device comprises a nebulizer, a humidifier, a vaporizer, or an inhaler.

The disclosure provides a method of maintaining or restoring metabolic function in a cell, comprising contacting the cell and a composition of the disclosure under conditions suitable for the composition to traverse a membrane of the cell, thereby maintaining or restoring metabolic function in the cell. In some embodiments, the cell is contacted in vitro, ex vivo, or in vivo.

The disclosure provides a method of maintaining or restoring metabolic function in a cell, comprising contacting the cell and a formulation of the disclosure under conditions suitable for the formulation to traverse a membrane of the cell, thereby maintaining or restoring metabolic function in the cell. In some embodiments, the cell is contacted in vitro, ex vivo, or in vivo.

The disclosure provides a method of reducing or preventing infection of a cell, comprising contacting the cell and a composition of the disclosure under conditions suitable for the composition to traverse a membrane of the cell, thereby reducing or preventing infection of the cell. In some embodiments, the cell is contacted in vitro, ex vivo, or in vivo.

The disclosure provides a method of reducing or preventing infection of a cell, comprising contacting the cell and a formulation of the disclosure under conditions suitable for the formulation to traverse a membrane of the cell, thereby reducing or preventing infection of the cell. In some embodiments, the cell is contacted in vitro, ex vivo, or in vivo.

The disclosure provides a method for treating a disease or disorder, comprising administering to a subject a therapeutically effective amount of a composition of the disclosure.

The disclosure provides a method for treating a disease or disorder, comprising administering to a subject a therapeutically effective amount of a formulation of the disclosure.

In some embodiments of the methods of the disclosure, treating comprises reducing a severity of at least one sign or symptom of the disease or disorder. In some embodiments, the disease or disorder is a loss of homeostasis of cellular metabolism. In some embodiments, the disease or disorder comprises at least one cell, cell type, tissue, or organ presenting an anaerobic cellular state. In some embodiments, the disease or disorder comprises an infectious disease, a proliferative disorder, an inflammatory disorder, a neurological disorder, a metabolic disorder, a cardiovascular disorder, a respiratory disorder, a blood-related disorder, a genetic disorder, an epigenetic disorder, a muscular disorder, a endocrine disorder, a hormonal disorder, a digestive disorder or a disorder secondary to a medical procedure or injury. In some embodiments, the disorder comprises Lyme Disease. In some embodiments, the disorder further comprises a disorder secondary or co-morbid with Lyme Disease. In some embodiments, the disorder is an infection. In some embodiments, the infection is a viral infection. In some embodiments, the infection is mediated by a coronavirus. In some embodiments, the infection is mediated by SARS-COV2. In some embodiments, the disorder comprises Hepatitis C. In some embodiments, the disorder comprises African Swine Fever. In some embodiments, the disorder comprises a tumor or a cancer. In some embodiments, the disorder comprises a wound from a medical procedure or an injury.

The disclosure provides a method for maintaining or restoring cellular metabolic homeostasis, comprising administering to a subject a therapeutically effective amount of a composition of the disclosure.

The disclosure provides a method for maintaining or restoring cellular metabolic homeostasis, comprising administering to a subject a therapeutically effective amount of a formulation of the disclosure.

In some embodiments of the methods of the disclosure, the composition is administered systemically. In some embodiments, the composition is administered orally, intranasally, intravenously, intraperitoneally, subcutaneously or intramuscularly.

In some embodiments of the methods of the disclosure, the composition is administered locally. In some embodiments, the composition is administered topically, intraocularly, intraspinally, intracerebroventricularly, intraosseously or intratumorally.

In some embodiments of the methods of the disclosure, the formulation is administered systemically. In some embodiments, the formulation is administered orally, intranasally, intravenously, intraperitoneally, subcutaneously or intramuscularly.

In some embodiments of the methods of the disclosure, the formulation is administered locally. In some embodiments, the formulation is administered topically, intraocularly, intraspinally, intracerebroventricularly, intraosseously or intratumorally.

The disclosure provides a method of conditioning an environment, comprising contacting a composition of the disclosure or a formulation of the disclosure and an element of the environment, wherein the conditioning reduces a measured value of a feature of a pathogen on the element when compared to a threshold value of the feature. In some embodiments, the element comprises one or more of a manmade material, a naturally-occurring material, a surface, a sub-surface, an interface, an area, a volume, an interior and an exterior. In some embodiments, the element comprises one or more of a portable object, a medical object, an edible object, a food object, a plant and an animal. In some embodiments, the element interacts with one or more of soil, air, atmosphere, and water. In some embodiments, the element comprises one or more of soil, air, atmosphere, and water. In some embodiments, the environment comprises a terrestrial environment or an aquatic environment. In some embodiments, the aquatic environment comprises one or more of an ocean, a river, a stream, a lake and a reservoir. In some embodiments, the feature of a pathogen comprises one or more of an abundance, a function, an activity, a virulence, a level of infectivity, and a rate of infectivity. In some embodiments, the pathogen comprises one or more of a virus, a bacteria, a fungus, a protozoa, an amoeba, a microbe, a worm and an insect.

The disclosure provides a composition and formulation for treating and mitigating diseases while bolstering metabolism of healthy cells includes at least one mineral cation bound by a hexa-aqua ligand complex and at least one ionic salt in a pharmaceutically acceptable carrier. The mineral cation hexa-aqua complex and ionic salt composition may further be combined with other pharmaceutically acceptable carriers for delivery with other ingredients.

In some embodiments, the composition and formulation as manufactured provides a delivery system for moving the mineral cation hexa-aqua complex and ionic salt to the target area of a cell. The ligand complex enables the functional properties of the cationic minerals without compromising the effectiveness and structure of the complex. Thus, it is able to travel throughout the body until it reaches the target cells where the ionic contents are then released into the cells. The composition allows for appropriate delivery of agents that are able to disrupt metabolic function of diseased and/or dysfunctional cells, while simultaneously impacting the metabolic homeostasis of healthy cells in a positive manner. It must be stressed that all minerals discussed can be introduced to the target cells using the hexa-aqua complex delivery system without the aid of additional compositions. The bioavailable mineral cation hexa-aqua complex and ionic salt composition is highly effective, but the use of botanicals, vitamins and mineral supplements, and formulation additives improve the performance of the mineral cation hexa-aqua complex and ionic salt composition alone.

The composition and delivery mechanism may be used to treat a myriad of organismal conditions including infection or infectious disease, proliferative disorder, inflammatory disorder, neurological disorder, traumatic tissue injury, and any ailment or dysfunction resulting from anaerobic or atypical cellular metabolism. Additionally, the composition and delivery system may be used in nutrition related problems, and bring cells to a state of metabolic homeostasis. Thus, the composition may be used for the general well-being of persons on a daily basis taking into account factors such as, sex, stress factors, genetics, and the environment. Moreover, the composition may be used to mitigate or prevent accumulation of pathogens in the terrestrial environment, on objects, or within food products.

The composition may take a plurality of different forms each having a different bioavailable cationic mineral or minerals, and ionic salt or salts in the same or different proportions. Different mechanisms for administering the mineral cation hexa-aqua complex and ionic salt composition may be used to ensure the bioavailable ionic contents reach the target area. For example, the mineral cation hexa-aqua complex and ionic salt composition may be introduced into the body of a subject (organism) by at least one of ingestion, inhalation, injection, capsules, suppository, transdermal patches, and cream or suave for use as a topical application. In certain embodiments, the subject may be a human. In another embodiment, subject may me a mammal. In another embodiment, the subject may be a plant.

The disclosure provides a composition for mitigating pathogens, treating diseases, and bolstering or maintaining cellular metabolic homeostasis includes a therapeutically effective amount of a mineral cation hexa-aqua complex and ionic salt in a pharmaceutically acceptable carrier. The cationic mineral, or minerals, of the mineral cation hexa-aqua complex and ionic salt composition are bound in a hexa-aqua complex enabling transport of said ionic contents through a biological system to a target cell. The mineral cation of the mineral cation hexa-aqua complex and ionic salt composition may be at least one of, or any combination of, actinium, bohrium, cadmium, chromium, cobalt, copernicium, copper, darmstadtium, dubnium, gold, hafnium, hassium, iridium, iron, lanthanum, magnesium, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be at least one of, or any combination of, actinium, cadmium, chromium, cobalt, copper, gold, hafnium, iridium, iron, lanthanum, manganese, mercury, molybdenum, nickel, niobium, osmium, palladium, platinum, rhenium, rhodium, ruthenium, scandium, seaborgium, silver, tantalum, technetium, titanium, tungsten, vanadium, yttrium, zinc, or zirconium that are able to form hexa-aqua complexes. In another embodiment, the mineral cation of the mineral cation hexa-aqua complex and ionic salt composition may be at least one of, or any combination of, chromium, cobalt, copper, gold, iron, manganese, magnesium, molybdenum, nickel, platinum, silver, vanadium, or zinc and all other forms of these minerals that are able to form hexa-aqua complexes. In another embodiment, the mineral cations of the mineral cation hexa-aqua complex and ionic salt composition may be copper, magnesium, and zinc. In certain embodiments, the ionic salt of the mineral cation hexa-aqua complex and ionic salt composition may be at least one of bicarbonate, calcium, chloride, sodium, sulfur, nitrogen, phosphorous, and potassium. In other embodiments, the ionic salts of the mineral cation hexa-aqua complex and ionic salt composition may be ammonium and hydrogen sulfate. In certain embodiments, the pharmaceutically acceptable carrier of the mineral cation hexa-aqua complex and ionic salt composition may be at least one of sugars, starches, cellulose or cellulose-derivatives, powdered tragacanth, malt, gelatin, talc, excipients, oils, glycols, polyols, esters, agar, alginic acid, pyrogen-free water, isotonic saline, Ringer's solution, ethyl alcohol, phosphate buffer solutions, cream, emulsion gel, liposome, nanoparticle, ointment, and other non-toxic comparative substances employed in pharmaceutical formulations. In other embodiments, the pharmaceutically acceptable carrier of the mineral cation hexa-aqua complex and ionic salt composition may be water.

Mineral cation ligands can be classified as metal coordination complexes and can be a versatile platform for design of novel compositions with quite different properties from those of purely organic compounds. The metals are selected for their variable oxidation states, coordination numbers and ability to bind to a wide variety of salts including sulfur, nitrogen, phosphorus and potassium. Such complexes can be utilized in many formulations directed at other higher organism health. The cationic minerals are associated with amines at inception during the manufacturing process and transition into hexa-aqua ligands leaving the nitrogen and hydrogen.

The disclosure provides a method for producing a mineral cation hexa-aqua complex and ionic salt composition for treating and mitigating disease while also bolstering metabolic homeostasis of healthy cells, comprising forming hexa-coordinated complexes with one or more cationic minerals by dissolving one or more ionic salts in water, wherein the composition comprises at least one cationic mineral complex encapsulated by hexa-aqua ligands. In some embodiments, amines attached to metal ions which are slowly absorbed as the ligand structure moves toward water ligands establishing a hexa-aqua complex and freeing up the amines for assimilation along with other antioxidants including hydrogen, and sulfur and nitrogen salts. In certain embodiments, other formulations may include other salts that comprise phosphorous, nitrogen, potassium, sodium, chloride, calcium, and/or bicarbonate in combination with other metals. A prepared mixture includes at least one organic mineral complex encapsulated by hexa-aqua ligands. In some embodiments, the one or more cationic minerals comprise chromium, cobalt, copper, gold, iron, manganese, magnesium, molybdenum, nickel, platinum, silver, vanadium, and zinc. In some embodiments, the one or more ionic salts comprise nitrogen, phosphorous, potassium, sulfur, and hydrogen. In certain embodiments, a diluted mixture may be combined with a pharmaceutically acceptable carrier for delivery with other ingredients.

In some embodiments, preparing the composition includes generating a solution of ammonium hydrogen sulfate using sulfuric acid (without pH buffering), diluting the ammonia hydrogen sulfate with water to form a mixture; adding specific minerals from the designated selection to the mixture in a salt form; and agitating the mixture comprising the ammonium hydrogen sulfate, sulfuric acid, water, and the mineral salt ingredients. In certain embodiments, other salts may be incorporated in the beginning formulation, or other formulations, with other minerals utilizing the basic concept as described above with substitution of the salt preparation.

In some embodiments, generating a solution of ammonium hydrogen sulfate comprises in the following order, a) mixing ammonium sulfate with distilled water; and b) mixing sulfuric acid with the mixture comprising ammonium sulfate and distilled water, wherein the components of said mixture are added at a rate that does not result in an exothermic reaction in excess of 300° C. during either a) or b). In some embodiments, the concentration of ammonium sulfate used in generating the solution of ammonium hydrogen sulfate is about 20% w/v or less. In some embodiments, the ammonium sulfate used in generating the solution of ammonium hydrogen sulfate is mixed with distilled water at a ratio of 3:2 or less, ammonium sulfate to distilled water. In some embodiments, the ammonium sulfate used in generating the solution of ammonium hydrogen sulfate is mixed with distilled water at a ratio of 1:1 or less, ammonium sulfate to distilled water. In some embodiments, the concentration of sulfuric acid used in generating the solution of ammonium hydrogen sulfate is about 18 M. In some embodiments, the sulfuric acid used in generating the solution of ammonium hydrogen sulfate is mixed with the mixture comprising ammonium sulfate and distilled water at a ratio of 1:1 or more, sulfuric acid to mixture comprising ammonium sulfate and distilled water. In some embodiments, the sulfuric acid used in generating the solution of ammonium hydrogen sulfate is mixed with the mixture comprising ammonium sulfate and distilled water at a ratio of 2:1 or less, sulfuric acid to mixture comprising ammonium sulfate and distilled water. In some embodiments, the mixture comprising ammonium sulfate, distilled water, and sulfuric acid is cooled to a temperature of less than 65.5° C. prior to adding one or more cationic minerals. In some embodiments, the one or more cationic minerals are added so that the ratio of minerals is optimized for bioavailability and avoidance of adverse mineral interactions of a biological system. In some embodiments, the one or more cationic minerals are added to the mixture of ammonium sulfate, distilled water, and sulfuric acid at ratio of at least 1:1:1, wherein the one or more cationic minerals are zinc, copper, and magnesium. In some embodiments, the one or more cationic minerals are added to the mixture of ammonium sulfate, distilled water, and sulfuric acid at a ratio of no more than 3:1:1, wherein the one or more cationic minerals are zinc, copper, and magnesium. In some embodiments, the method further comprises combining the composition comprising ammonium hydrogen sulfate, sulfuric acid, water, and one or more cationic minerals with a pharmaceutically acceptable carrier. In some embodiments, the method further comprises combining the composition comprising ammonium hydrogen sulfate, sulfuric acid, water, and one or more cationic minerals one or more botanical agent(s). In some embodiments, the one or more biological agent(s) comprises Graviola (*Annona muricate*), Bitter Melon (*Momordica charantia*), Esplanheira Santa (*Maytenus illcifolia*), Mullaca (*Physolis angulate*), Vasourinho (*Scoparia dulcis*), Mutamba (*Guazuma ulmifola*), Suma (*Pfaffia paniculata*), Cat's Claw (*Uncaria tomantosa*) and Blood Root (*Sanguinaria canadensis*).

In some embodiments of the present disclosure the combination of an acidic base with one or more selected minerals optimizes the availability of the mineral(s) in appropriate purity levels for the targeted disease, condition, indication or symptom. Thus, in some embodiments of the present disclosure, the resulting combined mixture optimizes the availability of the mineral(s) (both individually and in a combined mixture) for the treatment of a disease, condition, indication or symptom.

DETAILED DESCRIPTION

Organisms (humans, animals, and plants) are frequently subject to malnutrition and disease. Moreover, organisms experiencing states of malnutrition are at greater risk of contracting, developing, or perpetuating a disease or disorder. Macronutrients, micronutrients, and trace minerals help facilitate homeostasis of cellular metabolic functionality.

Acquisition of these nutrients is primarily accomplished through dietary intake, however access to food and nutrients, and appropriate balance of nutrients, is often limited and unmet. A variety of methods are used to supplement diet, but at unsatisfactory levels. Over-the-counter vitamins and minerals may be used, however, the levels of nutrient bioavailability in these supplements are inadequate.

Current methods of nutrient supplementation often utilize compounds that are minerals bound as oxides and salts. Both the minerals and salts are processed in the digestive system of a subject and must be split into ionic states through the processes of digestion. Moreover, the physiological process involving splitting the mineral from the salt results in an inefficient energy cost and subsequently a more limited degree of acquisition and use of nutrients. Thus, alternative methods of nutrient delivery are important to better manage malnutrition and disease.

Cells under diseased or dysfunctional states utilize bioavailable nutrients differently from that of healthy cells. Therefore, it is also desirable to generate nutrient-based compounds for use against a wide variety of diseases using a delivery system ensuring that associated compounds reach the intended target cells.

The invention is related to a mineral cation hexa-aqua complex and ionic salt composition for treating and mitigating diseases as well as bolstering or maintaining metabolic function of healthy cells. More particularly, the present disclosure relates to a composition having bioactive elements that are able to interrupt the metabolic pathway of cells presenting with disease or disease-provoked atypical metabolism while also positively impacting the metabolic pathway of healthy cells.

Minerals and Cellular Metabolism

Cationic mineral ligands and ionic salts are the result of a manufacturing process resulting in mineral ligands bound by six water molecules. The ligands act independently of one another in formulation. This allows the ionic salts and cationic minerals the ability combine with other molecules immediately. This capability provides a new tool to science for metal therapeutic compositions that can be used in new formulations.

Transition metals may be used in the mineral cation hexa-aqua complex and ionic salt composition. In certain embodiments, transition metals for use in the mineral cation hexa-aqua complex and ionic salt composition may include, but are not limited to, elements such as chromium, cobalt, copper, gold, iron, manganese, magnesium, molybdenum, nickel, platinum, silver, vanadium, and zinc. Minerals such as these may function in various biological processes, for example, cell metabolism and performing the cell cycle.

Nutrients that are essential to biological function include, but are not limited to, sodium, chloride, potassium, calcium, phosphorus, magnesium, sulfur, iron, zinc, iodine, selenium, copper, manganese, fluoride, chromium, molybdenum, nickel, silicon, vanadium, and cobalt. In certain embodiments, the mineral cation hexa-aqua complex and ionic salt composition may comprise one or more of sodium, chloride, potassium, calcium, phosphorus, magnesium, sulfur, iron, zinc, iodine, selenium, copper, manganese, fluoride, chromium, molybdenum, nickel, silicon, vanadium, and cobalt. Other biologically important elements include carbon, nitrogen, hydrogen and oxygen that can be absorbed from the air while other nutrients must be acquired (traditionally through absorption in the stomach) including water and other minerals. In certain embodiments, the mineral cation hexa-aqua complex and ionic salt composition may comprise one or more of carbon, nitrogen, hydrogen, and oxygen. In certain embodiments, the mineral cation hexa-aqua complex and ionic salt composition may comprise one or more of sodium, chloride, potassium, calcium, phosphorus, magnesium, sulfur, iron, zinc, iodine, selenium, copper, manganese, fluoride, chromium, molybdenum, nickel, silicon, vanadium, cobalt, carbon, nitrogen, hydrogen, and oxygen.

Nutrients (elements) play key roles in numerous biological functions. The following are provided as general non-limiting examples of how nutrients influence biological mechanisms.

Calcium plays a role in things such as bone and tooth development, enzyme activity, blood pressure regulation, muscle contraction, neuronal signaling, and blood clotting. Carbon plays a role in such things as acting as the primary component of macromolecules in biological systems. Chloride plays a role in things such as fluid regulation, blood pressure, and pH regulation. Chromium plays a role in things such as blood sugar regulation, and carbon metabolism. Cobalt plays a role in things such as cell division, amino acid synthesis, and co-enzyme functionality. Copper plays a role in things such as general metabolism, red blood cell formation, neurotransmitter regulation, and reduction of free radicals. Fluoride plays a role in things such as bone and tooth structural maintenance. Iron plays a role in things such as red blood cell functionality, amino acid synthesis, collagen synthesis, neurotransmitter synthesis, and hormone synthesis. Hydrogen plays a role in things such as formation and structure of macromolecules, and metabolic functionality. Iodine plays a role in things such as hormone synthesis and general metabolism. Nitrogen plays a role in things such as amino acid synthesis. Magnesium plays a role in things such as bone and tooth development, blood pressure regulation, muscle contraction, neuronal impulses, blood clotting, and enzyme functionality. Manganese plays a role in things such as amino acid metabolism, cholesterol metabolism, and carbohydrate metabolism. Molybdenum plays a role in things such as enzyme functionality, and removal of toxins. Nickel plays a role in such things as enzyme functionality and red blood cell maintenance. Oxygen plays a role in things such as signaling, metabolism, and cellular respiration. Phosphorus plays a role in such things as bone and tooth development, carbohydrate and lipid metabolism, and growth/maintenance and development. Potassium plays a role in things such as regulating fluids, maintain myocardial contractions, and general muscle contraction. Silicon plays a role in such things as collagen and elastin synthesis for development and maintenance of connective tissue. Selenium plays a role in things such as hormone regulation, nucleic acid synthesis, and cellular defense. Sodium plays a role in things such as regulating fluids, neuronal impulses, and muscle contraction. Sulfur plays a role in things such as protein synthesis, and antioxidant production. Vanadium plays a role in such things as immune response and growth factors. Zinc plays a role in things such as amino acid and nucleic acid biosynthesis, immune system functionality, and cellular division.

It is important to recognize that these nutrients (elements) interact with each other in biological systems. Elements in a biological system can impact or influence other (one or more) elements in a biological system in a dynamic fashion. Too much of one element (e.g., mineral) may easily disrupt equilibriums of other elements (e.g., other minerals) necessary to perform biological function. The phenomenon of mineral interactions has been well documented. Generally available mineral interaction charts provide indications of the interaction relationships between and among the minerals being combined in order to determine appropriate optimized mixtures of the minerals in the compositions of the present disclosure. For example, as shown by (O'Dell, B., Mineral Interactions Relevant to Nutrient Requirements, *J Nutrition,* 1989. 119:12 pp. 1832-1838) the mineral nutrient pairs comprising sodium-potassium, calcium-magnesium, manganese-iron, iron-copper, and zinc-copper all present with potential negative interactions with one and other when out of balance, as these particular interactions have been shown to influence the uptake and/or status of one and other. Using such information and the present disclosure, one skilled in the art can identify the selection of minerals and the exact mineral ratios for use in the compositions and/or formulations of the instant disclosure to optimize treatment of any specific disease, condition, indication or symptom without negatively disrupting intrinsic elements present in a biological system. The combining of a base, such as an acidic base, with the minerals can be repeated for multiple mineral additions based on the mineral interaction charts requirements and the specific disease, condition, indication or symptom. For such information, see also, e.g., Interactive Nutrition Facts Label, Vitamins and Minerals Chart 1, U.S. Food & Drug Administration, March 2020; B. L. O'Dell, Mineral Interactions Relevant to Nutrient Requirements, J Nutr. 119(12 Suppl):1832-1838, December 1999; Advanced Nutrition and Human Metabolism $6^{th}$ Ed., S. S. Gropper and J. L. Smith, Cengage Learning, Jun. 1, 2012, 608 pages; and, Advanced Nutrition: Macronutrients, Micronutrients, and Metabolism $3^{rd}$ Ed., C. D. Berdanier and L. A. Berdanier, CRC Press, Jul. 7, 2021, 592 pages. Therefore, it is imperative that nutrients in a biological system remain balanced to allow for optimal functionality.

Thus, when introducing ectopic minerals to a biological system careful consideration must be taken to generate positive outcomes while mitigating any negative effects that may occur as a result of inappropriately balanced nutrients. The phenomenon of mineral interactions is believed to spawn from instances where elements that may share common chemical parameters may compete for common metabolic sites. Mineral interactions and mineral balance may be exclusive to an independent biological system, each requiring specific parameters of particular minerals. The mineral cation hexa-aqua complex and ionic salt composition of the instant invention is tailored to maximize efficacy of mineral ion delivery, wherein the mineral contents are balanced in such a way as to mitigate any potential consequence of unfavorable mineral interactions (e.g., that may lead to deleterious biological responses), while still being effective in treating organisms infected with a pathogen or experiencing a disease pathology (e.g., cancer), and simultaneously bolstering or maintaining metabolism of healthy cells.

As previously stated, nutrients (elements) play a significant role in numerous biological functions, one of which being cellular respiration. Cellular respiration is the metabolic pathway by which cells procure energy. Cellular respiration in higher organisms may involve several metabolic pathways: (1) glycolysis, (2) pyruvate oxidation, (3) citric acid cycle, and (4) oxidative phosphorylation. Glycolysis occurs in the cytosol of cells and functions by breaking down glucose and generating pyruvate, ATP, and NADH. Pyruvate oxidation occurs in the mitochondrial matrix where pyruvate from glycolysis is converted into Coenzyme A (acetyl CoA), $CO_2$ is released, and NADH is generated. The citric acid cycle occurs in the mitochondrial matrix where acetyl CoA from pyruvate oxidation undergoes a series of cyclical reactions releasing $CO_2$, and generating ATP, NADH, and $FADH_2$. The charged energy carriers (NADH and $FADH_2$) are then used in oxidative phosphorylation in mitochondria where carrier molecules transfer electrons through an electron transport chain allowing for protons present in the matrix to build up in the intermembrane space forming a concentration gradient sufficient to generate ATP by flowing back to the matrix through an enzyme called ATP synthase, wherein oxygen accepts electrons and takes up protons to form water.

While only oxidative phosphorylation directly requires oxygen, both pyruvate oxidation and the citric acid cycle require oxidative phosphorylation to operate. Glycolysis is the only cellular respiration metabolic pathway, of the four previously listed cellular respiration metabolic pathways, that can occur without oxygen. When glycolysis takes place without oxygen it undergoes a slightly different process referred to as fermentation. For example, lactic acid fermentation is a process similar to glycolysis (as glucose is broken down), however the resulting pyruvate is further converted to lactate by oxidizing NADH to $NAD^+$, where $NAD^+$ may be recycled and once more used for either glycolysis or lactic acid fermentation. The process of fermentation is relatively quick, however produces less net ATP than if oxidative phosphorylation were to run to completion.

The Kreb's cycle (citric acid cycle) is a metabolic pathway of higher order organisms where the parallel use of available fuels, oxygen, water, and other essentials to life in an aerobic world follow the same basic metabolism of the sugars, fats and proteins to form a structure. The basic oxygen driven metabolism drives the continuation of both animals and higher plants. The metabolic system is a well-documented and familiar process involving the basic steps to produce a "higher" form of life. The protection provided by at least thirty-two steps in the process provides a system that protects the oxygen driven animals and plants. The basic knowledge we are incorporating in the instant invention can defeat lower order organisms, including diseases because the diseases follow a different metabolic pathway.

Lower order organisms are not nearly as complex regarding the metabolic pathway as the higher organisms (e.g., human or tree). Some prokaryotes perform aerobic or anaerobic metabolism, or switch between the two. Some prokaryotes utilize special enzymes and pathways that allow them to metabolize nitrogen or sulfur containing compounds, wherein in some instances nitrogen or sulfur containing compounds may be used as the final electron acceptor in the electron transport chain. The cycle followed by the lower order pathogens such as bacteria and fungi follow a less complicated process that allows the disease to multiply at an almost exponential rate based on available resources in an anaerobic cycle that has far fewer steps. The pathogens utilizes all available minerals, sugars, fats and proteins to fuel the reproduction of cells using the abbreviated anaerobic cycle; subsequently the higher the rate of replication, the less oxygen available for healthy tissues surrounding the disease. Reduced oxygen aids in the fermentation process that is part of the favorable conditions required for the exponential growth of all organisms using the anaerobic cycle, including cancer.

Furthermore, cells infected by various pathogens, or experiencing diseased pathology (e.g., cancer), have been shown to influence or alter a 'host' cell's basal metabolism. An example of this altered metabolism is exhibited by said pathogen-afflicted or diseased-afflicted cells by the visualization of increased glucose uptake and fermentation of glucose. It is believed that this occurs to promote growth, survival, proliferation, and long-term maintenance of the afflicted or diseased cell(s). This particular metabolic alteration is known as the Warburg Effect.

Pathogens affecting higher organisms have an advantage because of their ability for exponential growth due to the use of their shorter metabolic pathway versus the Krebs cycle. Similarly, cells infected with a pathogen or cells with a disease pathology (e.g., cancer) often alter the metabolism of the cell to be more amenable for the persistence of the pathogen or disease. The mineral cation hexa-aqua complex and ionic salt composition exploits the flaw in the exponential expansion of the pathogen and/or altered metabolism of the afflicted cell. Specifically, the flaw in pathogen or the afflicted cell is exploited by using the mineral gathering mechanism of the pathogen or afflicted cell against itself. Lower order organisms (e.g., pathogens) gather the necessary minerals and other building blocks in an amount proportional to their availability in the environment. Moreover, cells experiencing altered metabolism by means of pathogen infection or disease pathology, often exhibit dysregulation of ion channels which may allow for the inappropriate accumulation of ionic material. Both the metabolism exhibited by pathogens and the altered metabolism from infected or diseased cells differs from the metabolic processes exhibited by healthy cells from higher organisms which only accumulate, or appropriately regulate/maintain, enough of the elements and building blocks to satisfy the requirements of cellular respiration, particularly the Kreb's cycle.

Thus, the cells of higher organisms will only incorporate compositions of the disclosure at a rate necessary for survival and lower organisms (including pathogens), as well as infected and diseased cells will accumulate minerals in an amount that is toxic. Therefore, providing a high concentration of ionic minerals to an infection or diseased area of a subject (higher organism) would result in a toxic level of the mineral cations to a pathogen, an infected cell, or a diseased cell and allow survival of healthy cells so long as the dosage rate of the mineral cations is below the toxic level for the subject. There is a toxic level for even higher order organisms, but the amount of the minerals can be calculated to destroy pathogens, infected cells, or diseased cells with little to no effect on the healthy cells of higher organism. Killing the disease, infection, or pathogen agent can occur at proper dosages of the mineral cations while the healthy cells of the subject would only gather the amount of mineral cations necessary to complete the Krebs Cycle and reject the excess minerals.

The use of highly bio-available mineral cation hexa-aqua complex and ionic salt composition at a rate that will kill pathogens, infected cells, and diseased cells without impairing the function of the higher organism provides the active complex of the composition. The ligand system transports all the minerals to the target areas in the organism (cells).

The ligand system may be enhanced by the production of an artificial super-oxide dismutase cycle and transported quickly through an extra-cellular process (especially Copper and Zinc) to cells. The composition introduces the artificial SOD to a diseased tissue where peroxide is produced (an oxygen production process) that will also aid in killing disease cells (e.g., cancer). The creation of the artificial SOD cycle causes the disease-causing organism to uptake an amount of ionic mineral that is toxic which results in death of the disease organism. Additionally, diseases such as cancer follow an anaerobic fermentation process and oxygen will destroy the anaerobic fermentation process thereby providing a secondary mechanism for destroying the disease. In certain embodiments, the composition may also contain sulfur that may further aid in destroying cancer and provide relief of pain caused inflammation or other inflammatory-related diseases. The prime mode of action are the mineral cations in a highly biologically available formulation carried by the ligand complex.

Other mineral formulations are not as bio-available and cannot pass through cellular tissues in the manner demonstrated by the mineral cation hexa-aqua complex and ionic salt compositions described herein. In addition to the cationic mineral hexa-aqua complex and ionic salt composition, may further include predetermined amounts of at least one of vitamins and botanicals. The vitamins and/or botanicals provide an extra measure for successful treatment of a disease or insuring wellbeing of the higher organism (e.g., cellular homeostasis).

The general principle of the mineral cation hexa-aqua complex and ionic salt composition is rapid entry into the aerobic biological system of an organism using a ligand carrier in an ionic form that penetrates and migrates toward an anaerobic disease system, if present. The product is capable of penetrating the barrier zone between the aerobic and anaerobic tissues if the disease is internal and usually encapsulated by a barrier consisting of mucous and a bacteria or virus. The unique quality of the formulation is the penetration of tissues (cell membranes) and the movement of large amounts of ionic content into intended cells. The accumulation of the large amounts of mineral becomes toxic to the anaerobic system and the disease-causing agents, infected cells, or diseased are terminated.

Like other higher organisms, plants are subject to the same general principals pertaining to the Krebs cycle. Again, the composition penetrates the membrane of the disease more readily than conventional preparations of minerals and the disease accumulates the mineral(s) to a toxic level, while surrounding healthy plant tissues are unaffected except at extremely high dosages.

Diseases have three vulnerable sites that may be attacked by treatment using the mineral cation hexa-aqua complex and ionic salt composition and methods described:
1. Penetrating the outer membrane of the pathogen, infected cell, or diseased cell,
2. Destroying the internal components that drive the cells metabolism, and
3. Destroying the gene pool that may provide a future defense (resistance) against the introduced sub stance.

Minerals that are not in the bioavailable form will not be able to eliminate or otherwise disable the disease cells because the minerals cannot pass through the membrane coating the outer surface of the disease and/or cannot travel extra-cellularly. The mineral cation hexa-aqua complex and ionic salt composition will attack all of the pathogen's vulnerable targets, as well as the infected or diseased cells because of the systemic capabilities of the composition. The cell membrane is easily traversed and possibly ruptured, the inner cell is compromised because of the Kreb's cycle (aerobic vs. anaerobic) as described above and the cell is rendered destroyed. Beyond destroying the pathogen, infected cell, or diseased cell, there will be no further deviations from the genetic code to produce new strains of pathogenic agents or diseased cells that may be resistant to the product. In fact, there are no known resistances to animal and/or plant disease using minerals as the primary source of treatment.

Mode of Operation

The mineral cation hexa-aqua complex and ionic salt composition uses ionic mineral complexes and ionic salts that are capable of penetrating through the body having little to no adverse effect on normal cells while destroying the diseased or dysfunctional cells and pathogenic agents. Further, the ionic mineral complexes are capable of penetrating cell membranes at a rapid pace and are appropriately managed by normal cells as they will not allow net accumulation (abnormally high concentration) of minerals, and are discharged as excessive without disrupting normal cell functions. The action of the ligand or SOD provides for extra-cellular transport of the minerals to the pathogen, infected cell, or diseased cell, where mineral toxicity occurs. The process of destruction of the pathogen, infected cells, or diseased cells is an overload of mineral ions and in some cases the added effect of oxidation of the anaerobic disease fermentation process.

Normal cells will die as a result of excessive exposure to almost any mineral. The composition involves the use of an appropriate amount of the mineral in an ionic mineral complex form that will cause a toxic effect to the pathogen, infected cell, or diseased cell while not reaching a toxic level in healthy cells.

Another mode of action examined as the possible method of destruction of cancer and other diseases is the effect of the mineral cation complex on bacteria or other pathogens or saprophytic organisms that surround and act to encapsulate the disease. High numbers of bacteria, etc. have been identified in protective membranes and may be responsible for the membranes existence. The mineral cation hexa-aqua complex and ionic salt composition having anti-microbial properties and the ability to freely move between and through cells is capable of reaching the interface between healthy and diseased tissues and destroying the pathogenic agents. These properties may also be beneficial for penetrating protective membranes found in other diseases (e.g., cancer).

The mineral cation hexa-aqua complex and ionic salt composition is capable of destroying disease agents, and infected or diseased cells, wherein the body then removes said agents or cells (sheath like mass). The composition is capable of penetrating any sheath to the bacteria, and dissociate the sheath. The interior of the sheath contains the disease or pathogen agent (including cancer) and the natural immune system, if intact, will reject the mass of cells contained in the sheath which may include bacteria, virus, or other disease-causing agents contained within in a mass of cells that can move from an internal area of the body to be expelled. The sheath is the mass created by the accumulation of millions of white blood cells that accumulate around the destroyed diseased tissue that are separated from healthy tissue at the interface where the bacteria, virus, other disease agent was located. Once dead, the interface containing the destroyed disease agent, infected cells, or diseased cell and white-blood cells are separated from the healthy tissue and the mass of tissue inside the sheath is expelled from the body.

In certain embodiments, the compositions and formulations described herein are formulated in a manner such that said compositions and formulations will be delivered to a cell in a therapeutically effective amount, as part of a prophylactic general health-supporting agent, a preventive agent, or a therapeutic treatment.

Examples of Diseases that Hay be Treated Using the Mineral Cation Hexa-Aqua Complex and Ionic Salt Composition The mineral cation hexa-aqua complex and ionic salt composition does not perform in a biased nature toward any particular disease or pathogen. The mineral cation hexa-aqua complex and ionic salt composition allows for delivery of cationic minerals and ionic salts to cells of interest, wherein the cationic minerals and ionic salts traverse cellular membranes depositing said ionic contents within cells. Numerous pathogens, and atypical pathologies (e.g., cancer), are known to alter the physiology of the host cells, allowing for an environment amenable for proliferation of said pathogen, or atypical pathology. The altered physiology can include a myriad of things including alteration of ion channel function and general metabolism. Due to these alterations the mineral cation hexa-aqua complex and ionic salt composition is able to traverse the cell membranes at a relatively high degree and dysregulate the alterations made by the pathogen, or pathology, wherein the cell is unable to manage said ions (e.g., removal from the cell), resulting in death of the host cell and/or pathogen. The disease-associated alterations present in pathogen-effected, or atypical pathology-effected cells, are not present in healthy unaffected cells; the mineral cation hexa-aqua complex and ionic salt composition may still permeate the cell membrane of these cells, however these cells are able to appropriately manage these ions (e.g., removal from the cell), only allowing for net ion delivery appropriate to maintain general function to healthy cells. In certain embodiments, the mineral cation hexa-aqua complex and ionic salt composition may be used to prevent or treat viral diseases, bacterial diseases, protozoan diseases, and fungal diseases in a host subject. In other embodiments, the mineral cation hexa-aqua complex and ionic salt composition may be used to destroy viral pathogens, bacterial pathogens, protozoan pathogens, and fungal pathogens outside of a host subject. In another embodiment, the mineral cation hexa-aqua complex and ionic salt composition may be used to prevent or treat cancer in a host subject. In another embodiment, the mineral cation hexa-aqua complex and ionic salt composition may be used to aid in tissue regeneration or wound healing. In another embodiment, the mineral cation hexa-aqua complex and ionic salt composition may be used to provide stable inclusion of necessary ions to healthy cells. The mineral cation hexa-aqua complex and ionic salt composition effectively manages disease by not only directly disrupting disease (e.g., pathogen or atypical pathology) present in a subject, but also maintains appropriate metabolic homeostasis of healthy cells, allowing for optimally functional metabolism, wherein a subject may be better suited to heal wounds or fight diseases intrinsically.

Certain diseases and pathologies do not have a well-established treatment or cure. Additionally, some diseases are difficult to identify or diagnose and subsequently result in challenging progression and difficult treatment. Several examples of these types of diseases are discussed herein, and may be of particular interest for treatment using the mineral cation hexa-aqua complex and ionic salt composition.

The invention is now described with reference to treatment of the following example diseases. These example diseases are provided for the purpose of illustration only and the invention should in no way be construed as being limited to these particular disease examples, but rather should be construed to encompass any and all variations which become evident as a result of the teaching provided herein.

Without further description, it is believed that one of ordinary skill in the art can, using the description provided herein, treat the following illustrative example diseases using the mineral cation hexa-aqua complex and ionic salt composition. The following working examples, therefore, specifically point out the preferred embodiments of the present invention, and are not to be construed as limiting in any way the remainder of the disclosure.

Lyme Disease

Lyme Disease is transmitted by the bite of various species of *Ixodes* ticks carrying the etiologic agent, a pathogenic *Borrelia* bacterium (a spirochete). Organisms of the *Borrelia burgdorferi* sensu lato group belong to the family Spirochaetaceae, genus *Borrelia*. There are at least 11 species in the *B. burgdorferi* complex and an unknown but large number of substrains. At least three genospecies of the *Borrelia burgdorferi* sensu lato group have been identified as pathogens *B. burgdorferi* sensu stricto, *B. afzelli*, and *B. garinii*. In addition, other species of *Borrelia* have been implicated as being causative pathogenic agents. The major reservoir of the infection in the United States is the white footed mouse, and the infection can be transmitted to many mammalian species, including various other forms of wildlife, e.g. Eastern chipmunks, dogs, cats, and humans.

Clinically, Lyme disease is a progressive disease with a wide array of manifestations. Early diagnosis and treatment is critical to prevent progression. Late disseminated infection can be associated with permanent damage to the nervous and musculoskeletal systems. Unlike most bacterial diseases that can be defined microbiologically by direct observation or culture of the pathogen, *B. burgdorferi* is difficult to culture or observe in clinical samples. Therefore, Lyme disease is defined indirectly. Erythema migrans (EM) rash is the classic marker for this infection at early stages. However, not all patients infected with pathogenic *Borrelia* develop EM In the absence of EM, the current basis for diagnosis is the demonstration of an antibody response against a pathogenic *Borrelia* in an appropriate clinical setting.

Sometimes Lyme disease can be cured with antibiotic treatment alone, especially when the treatment begins early in the course of illness. See, e.g., Tickborne Diseases of the United States, A Reference Manual for Health Care Providers, U.S. Dept of Health and Human Services, Centers for Disease Control and Prevention, Fourth Edition, 2017; Cameron et al., Evidence Assessments and Guideline Recommendations in Lyme Disease: the Clinical Management of Known Tick Bites, Erythema Migrans Rashes and Persistent Disease, Expert Review of Anti-infective Therapy, Vol. 12, Issue 9, 2014; Wormser et al., The Clinical Assessment, Treatment, and Prevention of Lyme Disease, Human Granulocytic Anaplasmosis, and Babesiosis Clinical Practice Guidelines by the Infectious Diseases Society of America, Clinical Infectious Diseases, Vol. 43, Issue 9, Pages 1089-1134, November 2006; and, Conquering Lyme Disease, Science Bridges the Great Divide, B. A. Fallon and J. Sotsky, Columbia University Press; Illustrated edition (Dec. 12, 2017), 456 pages. Unfortunately, only a fraction of Lyme patients are being treated due to equivocal clinical manifestations, inaccurate tests, and underreporting.

Lyme disease, if left untreated, can result in a large range of signs and symptoms. Such signs and symptoms can include EM rashes, swollen lymph nodes, arthritis and swelling of joints, carditis and heart arrhythmia, neuritis, neurocognitive impairment, facial palsy, intermittent pain or paresthesia of the body, fever, fatigue, dizziness, and shortness of breath.

The result of undiagnosed and untreated patients can lead to the development of Post-Treatment Lyme Disease Syndrome (PTLDS), where symptoms persist for a duration of time even after treatment occurs. Furthermore, if left untreated the disease can progress to late-stage developments such as chronic Lyme arthritis or chronic Lyme neuroborreliosis, which can have devastating consequences in certain cases.

Due to difficulty in diagnosis and early treatment, there is clearly a need for reliable treatment for those that have been infected with Lyme Disease as well as those who may contract Lyme Disease.

COVID-19

A new disease called coronavirus disease 2019 (COVID-19) recently emerged globally (Centers for Disease Control (CDC), 2020). COVID-19 illnesses have ranged from mild symptoms to severe illness and death. The World Health Organization declared the outbreak a Public Health Emergency of International Concern on 30 Jan. 2020, and a pandemic on 11 Mar. 2020. As of 10 Jul. 2020, over 12 million cases of COVID-19 (in accordance with the applied case definitions and testing strategies in the affected countries) have been reported, including over 500,000 deaths.

COVID-19 is caused by a strain of coronavirus called severe acute respiratory syndrome coronavirus 2 (SARS-CoV-2). SARS-CoV-2 was previously referred to by its provisional name, 2019 novel coronavirus (2019-nCoV), and has also been called human coronavirus 2019 (HCoV-19 or hCoV-19).

SARS-CoV-2 is a positive-sense, single-stranded RNA virus that is contagious in humans. Taxonomically, SARS-CoV-2 is a strain of severe acute respiratory syndrome-related coronavirus (SARS-CoV). It is believed to have zoonotic origins and has close genetic similarity to bat coronaviruses, suggesting it emerged from a bat-borne virus. The virus shows little genetic diversity, indicating that the spillover event introducing SARS-CoV-2 to humans is likely to have occurred in late 2019.

Epidemiological studies estimate that each COVID-19 infection results in 1.4 to 3.9 new ones when no members of the community are immune and no preventive measures taken. The virus is thought to primarily spread between people through close contact and via respiratory droplets produced from coughs or sneezes. It mainly enters human cells by binding to the receptor angiotensin converting enzyme 2 (ACE2).

Signs and symptoms of COVID-19 may range from fever, shortness of breath or difficulty breathing, fatigue, muscle or body aches, headache, loss of taste or smell, sore throat, congestion, nausea or vomiting, diarrhea, to respiratory failure, and death.

No vaccine or cure for COVID-19 currently exists. Treatments continue to develop with only varying success. Given the high rate of infectivity and mortality associated with SARS-CoV-2, there is clearly a need for reliable treatment for those that have been infected with SARS-CoV-2 as well as those who may contract COVID-19.

Hepatitis C

Infection by hepatitis C virus (HCV) is a compelling human medical problem. HCV is recognized as the causative agent for most cases of non-A and non-B hepatitis, with an estimated worldwide prevalence of 170 million cases as of the mid 1990s (i.e., 2-3%) (Choo et al., Science, 1989, 244:359-362; Kuo et al., Science, 1989, 244:362-364; Purcell, FEMS Microbiol. Rev., 1994, 14.181-192; Van der Poel, In: Current Studies in Hematology and Blood Transfusion, Reesink ed., Basel: Karger, pp. 137-163, 1994).

HCV is primarily transmitted parenterally, although sexual and perinatal transmission do appear to occur. At present, no risk factor has been identified in about 40% of HCV-infected individuals in the US (Alter, Infect. Agents Dis., 1993, 2:155-166). Upon first exposure to HCV, only about 10% or less of infected individuals develop acute clinical hepatitis, while others appear to resolve the infection spontaneously. In most instances, however, the virus establishes a chronic infection that persists for decades, leading in about 50% of all cases to chronic hepatitis, which can, in turn, develop into liver cirrhosis and/or hepatocellular carcinoma (Iwarson, FEMS Microbiol. Rev., 1994, 14:201-204; Kew, ibid. pp. 211-220; Saito et al., Proc. Natl. Acad. Sci. USA, 1990, 87:6547-6549).

Apart from liver cells, HCV can also replicate in peripheral blood mononuclear cells (PBMCs) both in vivo and in experimentally infected B- and T-cell lines (U.S. Pat. Nos. 5,679,342 and 5,968,775). Such a lymphotropism may account for the numerous immunological disorders, in particular type II and type III cryoglobulinaemia, observed in more than 50% of chronic hepatitis C patients (Esteban et al., In: Hepatitis C Virus, Reesink ed., Basel: Karge, 1998, pp. 102-118).

Signs and symptoms of hepatitis C range from bleeding and bruising easily, fatigue, poor appetite, yellow discoloration of the skin and eyes (jaundice), dark-colored urine, itchy skin, fluid buildup in the abdomen (ascites), swelling in legs, weight loss, confusion and slurred speech (hepatic encephalopathy), and spider angiomas, to liver failure and death.

Unlike hepatitis A and hepatitis B, currently there is no vaccine for hepatitis C. Hepatitis C treatment commonly involves using anti-viral medication. Given that acute hepatitis C infection usually goes undiagnosed, due to often asymptomatic presentation, there is clearly a need for reliable treatment for those that have been infected with hepatitis C as well as those who may contract hepatitis C.

African Swine Fever

African swine fever is a haemorrhagic disease of domestic pigs caused by a double-stranded DNA virus, African swine fever virus (ASFV). ASFV is the only member of the Asfarviridae family and replicates predominantly in the cytoplasm of cells. Virulent strains of ASFV can kill domestic pigs within about 5-14 days of infection with a mortality rate approaching 100%.

ASFV can infect and replicate in warthogs (*Phacochoerus* sp.), bushpigs (*Potamocherus* sp.) and soft ticks of the *Ornithodoros* species, but in these species few if any clinical signs are observed and long term persistent infections can be established. The disease is currently endemic in many sub-Saharan countries and in Europe in Sardinia. Following its introduction to Georgia in the Trans Caucasus region in 2007, ASFV has spread extensively through neighboring countries including the Russian Federation. In 2012 the first outbreak was reported in Ukraine and in 2013 the first outbreaks in Belarus. In 2014 further outbreaks were reported in pigs in Ukraine and detection in wild boar in Lithuania and Poland.

There is currently no treatment for ASF. Prevention in countries outside Africa has been attempted on a national basis by restrictions on incoming pigs and pork products, compulsory boiling of waste animal products under license before feeding to pigs and the application of a slaughter policy when the disease is diagnosed. Prevention in Africa is based on measures to keep warthogs and materials contaminated by warthogs away from the herd. Thus, there is thus a need for improved measures to control ASFV infection and prevent spread of the disease.

Cancer

Cancer is a disease, characterized by the development of abnormal cells that exhibit uncontrollable proliferation and the ability to permeate and damage normal body tissues. Cancer is notable for being one of the leading causes of death worldwide.

Signs and symptoms of cancer vary widely, often negatively influencing the function of the particular tissues the aberrant cells infiltrate.

Unfortunately, a cure for cancer has yet to be identified, however a number of various treatments do exist. Thus, a need for additional measures are needed to aid in cancer treatment or prevention.

Wound Management

Tissues often experience degrees of damage through various means (e.g., general wear and tear, trauma, surgical intervention). Tissue regeneration requires the physiological ability for cells to appropriately proliferate and return functionality to an affected area. Cells must undergo assimilate partitioning to correctly manifest new tissue, wherein nutrients and resources are appropriately allocated to cells to perform needed function (e.g., cellular respiration, protein metabolism, and nucleic acid metabolism). Thus, if a subject is lacking appropriate nutrients and resources, cells are at a disadvantage to regenerate tissues.

Not only can normal tissue regeneration and wound management be a difficult task, but it can also be exacerbated by complications that easily manifest during healing making treatment even more difficult. Such complications include, infection, osteomyelitis, tissue necrosis and gangrene, periwound dermatitis, edema and periwound edema, hematomas, and dehiscence which can result in chronic non-healing wounds. Treatment of wounds can often include treatment of secondary complications, vacuum granulation of tissue, tissue scaffolding, graft tissues, surgical intervention, haemoglobin spray, and hyperbaric oxygen therapy, to name a few. Thus, a need for additional measures are needed to aid in wound management Disease Mitigation by Application of the Composition Due to the mineral cation hexa-aqua complex and ionic salt composition mode of action, non-toxic nature on higher organisms, and ability to solubilize in water, the composition may be used as an agent that prevents the accumulation of, or mitigates, pathogens in an ex-vivo capacity. Contacting the mineral cation hexa-aqua complex and ionic salt composition with elements of the terrestrial environment, objects, or commercial foods may be an effective way in which to kill or render a pathogenic agent ineffective.

The mineral cation hexa-aqua complex and ionic salt composition of the present invention can be effective against pathogens in water and may be used at rates that are effective against higher organism pathogens. Post-harvest drenches of the product on fruits, vegetables, animal by-products, milk, eggs, poultry and other articles have been shown to harbor pathogens. In certain embodiments, the mineral cation hexa-aqua complex and ionic salt composition may be used to reduce or eliminate pathogens from post-harvest drenches. The compositions of the present invention may be capable of eliminating pathogens that threaten both animals and plants.

The mineral cation hexa-aqua complex and ionic salt composition may also be effective in reducing and/or eliminating pathogens that result during storage and handling of fish, shellfish, poultry, meat products of cattle, sheep, pigs and other animals. In certain embodiments, rinsing, dipping and/or washing, or by other means of treatment, of animal products using the mineral cation hexa-aqua complex and ionic salt composition may provide control and/or elimination of pathogens that affect higher organisms. The mineral cation hexa-aqua complex and ionic salt composition of the present invention may be effective in controlling and/or eliminating pathogens such as pathogenic bacteria, virions, fungi, protozoans and other diseases or pathogens of importance to the health of higher organisms when used in a similar manner.

The mineral cation hexa-aqua complex and ionic salt composition may be effective in controlling and/or eliminating storage pathogens in liquids such as, but not limited to, water, juices, milk, etc. In certain embodiments, the mineral cation hexa-aqua complex and ionic salt composition may be used to wash and coat, or by other means of treatment, food and non-food products, wherein the shelf life of said products may be extended by eliminating the storage diseases while not affecting the food and nonfood products.

In certain embodiments, the mineral cation hexa-aqua complex and ionic salt composition may be applied to animal and/or plant by-products such as water, milk, and milk by-products, juices and other liquids used in human and animal consumption to destroy pathogens and enhance food safety.

Furthermore, in certain embodiments, the mineral cation hexa-aqua complex and ionic salt composition and formulations thereof may be used to kill or destroy a pathogenic agent on environmental surfaces.

The mineral cation hexa-aqua complex and ionic salt composition can be used in aerosolized, misted, vaporized, fogged, humidified or other forms to produce micronized particles of the composition that can remain in suspension in the air for long periods of time. The micronized particles act much like a fumigant to provide total coverage to all sides of a surface that may be harboring pathogenic agents. In certain embodiments, the mineral cation hexa-aqua complex and ionic salt composition, in any form, may be able to intercept pathogenic agents (e.g., protozoans, bacteria, fungi, viruses), spores and/or resting (dormant) stages of pathogens in the air or on a surface, wherein said pathogenic agents are rendered ineffective. In certain embodiments, the mineral cation hexa-aqua complex and ionic salt composition prompts the pathogen to vegetate and/or otherwise vitalize the dormant stage, wherein the mineral cation hexa-aqua complex and ionic salt composition by itself or in combination with other components of a formulation capable of killing or rendering ineffective the vegetative stage and/or spores and/or resting spores and/or resting stage of a pathogen by contact and/or action of the composition on the pathogen.

In certain embodiments, the formulation of the mineral cation hexa-aqua complex and ionic salt composition includes inert ingredients such as, but not limited to surfactants, detergents or semiochemicals that may further affect the dormant stage of pathogens by acting on the cell walls or structure of the pathogen allowing the composition to kill the most resistant life stage of the pathogen. For example, the cell walls of bacteria or fungal spore are hydrophilic (attract and absorb water). In certain embodiments, the mineral cation hexa-aqua complex and ionic salt composition deployed in a micronized mist (which contains water) is attracted to the structure of the fungus and *Bacillus* and may be further compromised through the use of surfactants, detergents and/or semiochemicals, wherein the composition of the present invention is then able to kill or render ineffective the pathogenic agent. If bacterial spores or resting spores are coated with a hydrophilic material (such as gelatin) target pathogenic agents may be further encapsulated and enhance treatment using the mineral cation hexa-aqua complex and ionic salt composition. In certain embodiments, the mineral cation hexa-aqua complex and ionic salt composition may be applied to resting spores and/or to cell walls of the bacterium by mist using a hydrophilic coating, wherein the pathogen may be further compromised allowing the composition kill or render the pathogen agent ineffective.

The micronized particle may be used in any situation where air-borne pathogenic fungal spores and/or other vegetative or reproductive stages of pathogens are present. The composition of the present invention may therefore be used to eradicate highly refined pathogenic agents including animal and plant air-borne pathogens.

Additives to Composition

In certain embodiments, the mineral cation hexa-aqua complex and ionic salt composition may be formulated in combination with inerts that may include, but are not limited to additives such as surfactants, di-methyl sulfoxide (DSMO), detergents, hydroscopic compounds such as, but not limited to Cell-U-Wet, and/or other chemicals, to aid in penetration through the skin and/or for other reasons necessary in manufacture of formulations for ingestion, inhalation, injection, tablets, suppository, transdermal patches, etc.

Nebulization Formulation

In some embodiments, the composition is formulated to be administered through inhalation via nebulization or dispersed in droplet form. Formulation suitable for nebulization presents as an effective route of administration for delivery to the respiratory tract. This mechanism of delivery may be particularly helpful in combating novel respiratory diseases as well as functions as a quick acting systemic delivery route for the mineral cation hexa-aqua complex and ionic salt composition.

It should be noted that this is this an effective route of systemic administration, but is particularly useful for treatment of pathogens, infected cells, and diseased cells associated with the pulmonary system.

In some nebulizers, a gas and a fluid are mixed together and directed against a baffle or diverter. In some other nebulizers, interaction of the gas and fluid is enhanced through impacting the gas and fluid against a diverter. The term diverter, as used here, includes any baffle or impinger. As a result of either nebulization process described above, the fluid is transformed into an aerosol, that is, the fluid is caused to form small particles that are suspended in the air and that have a particle size in a range suitable for delivery to a targeted area of a patient's respiratory tract. One way to mix the gas and fluid together in a nebulizer is to pass a quickly moving gas over a fluid orifice tip of a tube. The negative pressure created by the flow of pressurized gas is a factor that contributes to drawing fluid out of the fluid orifice into the stream of gas and nebulizing it.

Effective and economical nebulizer therapy includes the ability to quickly generate a large amount of aerosol within a predetermined particle size range. An effective nebulizer preferably provides these features synchronously with the inhalation of the patient. In order to actuate a mechanical nebulizer, a patient's inhalation effort must overcome certain variables. Depending on the structural configuration of the nebulizer, these variables may include one or more of the following: the volumetric flow rate of the flowing gas; air leaks in the device; the force exerted by the flowing gas on a moveable diverter; and the friction between moveable parts. The greater the flow rate, air leaks and friction, the greater the inhalation effort required in order to actuate the device. It is desirable that a nebulizer have adequate sensitivity to quickly respond to an inhalation while not adversely restricting the patient's inhalation.

Various excipients and carriers may be used to increase effective delivery of nebulized therapeutics. Depending on the mechanism of action for nebulization and the components of the therapeutic, the use of tonicity adjusting agents, pH adjusting agents, buffering agents, purging agents, co-solvent agents, antimicrobial preservative agents, suspension agents, surfactant agents, and humectant agents can be warranted.

Agents specifically intended for nebulization may include one or more of tonicity adjusting agents including sodium chloride, and dextrose; pH adjusting agents including sodium hydroxide, hydrochloric acid, and sulphuric acid; buffering agents including sodium citrate, sodium phosphate, and citric acid; purging agents including nitrogen; co-solvent agents including alcohol, polyethylene glycol (PEG) 400, and propylene glycol; antimicrobial preservative agents including benzalkonium chloride, ethanol, propylene glycol, beczoyl alcohol, chlorobutanol, and methyl paraben; suspension agents including carboxymethylcellulose (CMC), and sodium CMC; surfactant agents including poractant, poracant alfa, polysorbate 80 and polysorbate 20; and humectant agents including glycerin. In certain embodiments, the mineral cation hexa-aqua complex and ionic salt composition may be formulated to be administered via nebulization or by droplet dispersion by including one or more of tonicity adjusting agents including sodium chloride, and dextrose; pH adjusting agents including sodium hydroxide, hydrochloric acid, and sulphuric acid; buffering agents including sodium citrate, sodium phosphate, and citric acid; purging agents including nitrogen; co-solvent agents including alcohol, polyethylene glycol (PEG) 400, and propylene glycol; antimicrobial preservative agents including benzalkonium chloride, ethanol, propylene glycol, beczoyl alcohol, chlorobutanol, and methyl paraben; suspension agents including carboxymethylcellulose (CMC), and sodium CMC; surfactant agents including poractant, poracant alfa, polysorbate 80 and polysorbate 20; and humectant agents including glycerin. In other embodiments, the mineral cation hexa-aqua complex and ionic salt composition may be formulated to be administered via nebulization or by droplet dispersion by not incorporating a tonicity adjusting agent, pH adjusting agent, buffering agent, purging agent, co-solvent agent, antimicrobial preservative agent, suspension agent, surfactant agent, or humectant agent.

Botanical Extracts and Isolations

Plants, plant extracts and isolations have been used for centuries to treat certain diseases in humans and promote general wellness. One major factor in the cure of diseases and wellness is boosting the immune system and, several plants are known to have ingredients that have shown support in helping to fight or prevent disease. The mineral ion zinc, may be used in coordination with certain plant extracts for boosting the immune system and combating certain diseases. For example, extracts may include any of the following but are not limited to: Graviola (*Annona muricata*), Bitter Melon (*Momordica charantia*), Esplanheira Santa (*Maytenus illcifolia*), Mullaca (*Physolis angulata*), Vasourinho (*Scoparia dulcis*), Mutamba (*Guazuma ulmifolia*), Suma (*Pfaffia paniculata*), Cat's Claw (*Uncaria tomantosa*), Blood Root (*Sanguinaria canadensis*). The quality of the botanical correlates to the performance of the plant extracts and a person trained in the art is necessary in most cases to provide a measure of success.

For example, not all Graviola trees will yield the same amount of the active ingredient from the leaves or fruit, and someone skilled in selection of the leaves from specific trees can provide a superior extract following a detailed recipe. For instance, only bottled water (not chlorinated) must be mixed with a specific surfactant before adding cinnamon and the plant material and cooked in stainless steel or glass for five days at 140-160 degrees F. and twice filtered before storage at room temperatures and in some embodiments the product is not taken with co-enzyme QlO (COQ10). Q10 which is a food supplement. The results are noteworthy when with the mineral cation hexa-aqua complex and ionic salt composition and other supplements including but not limited to vitamins and minerals.

Vitamin and Mineral Supplements

The use of mineral cation hexa-aqua complex and ionic salt composition may greatly improve general health, but not all minerals can be processed into a mineral cation hexa-aqua complex and ionic salt composition. Therefore, mineral supplements may be necessary in traditional forms to meet minimum daily requirements when boosting the strength of the immune system. It is true that the daily allowances for both vitamins and minerals can be obtained through a healthy diet, but when an individual's immune system is compromised and they are facing disease (e.g., cancer or some other major disease), supplementing the food intake is critical to the mitigation of the disease, or appropriate response and maintenance of the disease.

An example of a rigorous and effective regimen of vitamins and minerals for establishing cellular homeostasis and optimum functionality, but is not limited to the following:
MORNING
Beta Carotene (Vit. A)—25,000 I.U.
Vit. B-6—100 mg
COQ10 (Except with Graviola)—100 mg
Folic Acid—800 mg
Vit. D—400 I.U.
Selenium (Yeast)—200 mcg
Biotin—1000 mcg
Chromium Piconate—200 mcg
Multi-Vitamin (Organic) that contains Micro-Nutrients (Trace Elements)
EVENING
Aspirin (If Tolerant)—small (e.g., 75 to 150 mg)
Zinc Gluconate—250 mg
Magnesium Sterate—250 mg
Calcium Citrate—600 mg
Omega 3 (Fish Oil)—1000 mg
Red Yeast Rice—600 mg
Vit. E—400 I.U.
Ester Vit. C—1000 mg
Glucosamine Sulfate—500 mg
Chondrotin Sulfate—500 mg
Methylsulfonylmethane—200 mg The efficacy of the mineral cation hexa-aqua complex and ionic salt composition may be enhanced by using the composition in combination with botanicals and vitamins. In certain embodiments, use of botanicals and vitamins may be used in combination with mineral cation hexa-aqua complex and ionic salt composition to synergistically impact an organisms own cellular function manage infection and disease while also maintaining healthy cells. The mineral cation hexa-aqua complex and ionic salt composition provides a direct attack on the membrane sheath surrounding the cancer cells and a direct attack on the cancer itself by over-loading the cancer cells with minerals that become toxic to the cancer while not affecting the surrounding healthy tissues.

Modifications

The treatment of diseases such as cancers, for example, skin, colon, liver, prostate cancer may require different combinations of the ionic mineral complexes formulated with certain inerts and made for each specific application. In certain embodiments, the mineral cation hexa-aqua complex and ionic salt composition may also contain pharmaceutically acceptable carriers, diluents, cream bases, hydroscopic additives, detergents and/or other carriers required for the therapeutically effective dosage to travel to the specific target site for the intended purpose. In certain embodiments, mineral cation hexa-aqua complex and ionic salt composition may be therapeutically administered by at least one of topical, oral, inhalation, injection, rectally or other methods of application, in a therapeutically effective form of the formulation. Other diseases that can be mitigated by use of mineral cation complexes by themselves or in combinations of mineral cation complexes derived from the method of disassociation of compounds include, but are not limited to, arthritis or any other degenerative disease. The same systems of ionic minerals can be used for promoting wellness of an individual to facilitate disease resistance, increase energy, etc. Formulations for applying the active ingredient(s) include, but are not limited to, the above inert ingredients.

The mineral cation hexa-aqua complex and ionic salt composition may be tailored to incorporate various ionic materials that may be directed to enhance or treat dysfunctional innate biological functions. In certain embodiments, the mineral cation hexa-aqua complex and ionic salt composition may comprise calcium to be used to positively influence or treat dysfunction associated with bone and tooth development, enzyme activity, blood pressure regulation, muscle contraction, neuronal signaling, and blood clotting. In certain embodiments, the mineral cation hexa-aqua complex and ionic salt composition may comprise carbon to be used to positively influence or treat dysfunction associated with macromolecule formation or metabolism in biological systems. In certain embodiments, the mineral cation hexa-aqua complex and ionic salt composition may comprise chloride to be used to positively influence or treat dysfunction associated with fluid regulation, blood pressure, and pH regulation. In certain embodiments, the mineral cation hexa-aqua complex and ionic salt composition may comprise chromium to be used to positively influence or treat dysfunction associated with blood sugar regulation, and carbon metabolism. In certain embodiments, the mineral cation hexa-aqua complex and ionic salt composition may comprise cobalt to be used to positively influence or treat dysfunction associated with cell division, amino acid synthesis, and co-enzyme functionality. In certain embodiments, the mineral cation hexa-aqua complex and ionic salt composition may comprise copper to be used to positively influence or treat dysfunction associated with general metabolism, red blood cell formation, neurotransmitter regulation, and reduction of free radicals. In certain embodiments, the mineral cation hexa-aqua complex and ionic salt composition may comprise fluoride to be used to positively influence or treat dysfunction associated with bone and tooth structural maintenance. In certain embodiments, the mineral cation hexa-aqua complex and ionic salt composition may comprise iron to be used to positively influence or treat dysfunction associated with red blood cell functionality, amino acid synthesis, collagen synthesis, neurotransmitter synthesis, and hormone synthesis. In certain embodiments, the mineral cation hexa-aqua complex and ionic salt composition may comprise hydrogen to be used to positively influence or treat dysfunction associated with plays a role in things such as formation and structure of macromolecules, and metabolic functionality. In certain embodiments, the mineral cation hexa-aqua complex and ionic salt composition may comprise iodine to be used to positively influence or treat dysfunction associated with hormone synthesis and general metabolism. In certain embodiments, the mineral cation hexa-aqua complex and ionic salt composition may comprise nitrogen to be used to positively influence or treat dysfunction associated with amino acid synthesis. In certain embodiments, the mineral cation hexa-aqua complex and ionic salt composition may comprise magnesium to be used to positively influence or treat dysfunction associated with bone and tooth development, blood pressure regulation, muscle contraction, neuronal impulses, blood clotting, and enzyme functionality. In certain embodiments, the mineral cation hexa-aqua complex and ionic salt composition may comprise manganese to be used to positively influence or treat dysfunction associated with amino acid metabolism, cholesterol metabolism, and carbohydrate metabolism. In certain embodiments, the mineral cation hexa-aqua complex and ionic salt composition may comprise molybdenum to be used to positively influence or treat dysfunction associated with enzyme functionality, and removal of toxins. In certain embodiments, the mineral cation hexa-aqua complex and ionic salt composition may comprise nickel to be used to positively influence or treat dysfunction associated with enzyme functionality and red blood cell maintenance. In certain embodiments, the mineral cation hexa-aqua complex and ionic salt composition may comprise oxygen to be used to positively influence or treat dysfunction associated with signaling, metabolism, and cellular respiration. In certain embodiments, the mineral cation hexa-aqua complex and ionic salt composition may comprise phosphorous to be used to positively influence or treat dysfunction associated with bone and tooth development, carbohydrate and lipid metabolism, and growth/maintenance and development. In certain embodiments, the mineral cation hexa-aqua complex and ionic salt composition may comprise potassium to be used to positively influence or treat dysfunction associated with regulating fluids, maintain myocardial contractions, and general muscle contraction. In certain embodiments, the mineral cation hexa-aqua complex and ionic salt composition may comprise silicon to be used to positively influence or treat dysfunction associated with collagen and elastin synthesis for development and maintenance of connective tissue. In certain embodiments, the mineral cation hexa-aqua complex and ionic salt composition may comprise selenium to be used to positively influence or treat dysfunction associated with hormone regulation, nucleic acid synthesis, and cellular defense. In certain embodiments, the mineral cation hexa-aqua complex and ionic salt composition may comprise sodium to be used to positively influence or treat dysfunction associated with regulating fluids, neuronal impulses, and muscle contraction. In certain embodiments, the mineral cation hexa-aqua complex and ionic salt composition may comprise sulfur to be used to positively influence or treat dysfunction associated with protein synthesis, and antioxidant production. In certain embodiments, the mineral cation hexa-aqua complex and ionic salt composition may comprise vanadium to be used to positively influence or treat dysfunction associated with immune response and growth factors. In certain embodiments, the mineral cation hexa-aqua complex and ionic salt composition may comprise zinc to be used to positively influence or treat dysfunction associated with amino acid and nucleic acid biosynthesis, immune system functionality, and cellular division.

Complex Ion Formation/Ligand Bonds

The formation of the hexa-aqua complex is understood in chemistry as complex ion formation. The mineral cation acts as a central ion, where molecules attach to the central metal ion to form a complex. These molecules attaching to the central metal ion are considered ligands, wherein the ligands supply electrons by means of coordinate covalent bonding. Examples of simple ligands include water, ammonia, and chloride ions.

Ligands function as lone pair donors, and thus Lewis bases. Central metal ions that form a number of bonds with the ligands determine the coordination number, or total points of attachment to the central element, for the complex ion. Therefore, hexa-aqua complexes are metal aquo complexes using only water as a ligand forming six coordinate covalent bonds with a central metal ion.

The mineral cation hexa-aqua complex and ionic salt composition manufacturing process produces a complex having ammonia ligand bonds with specific cations. The cations are "encapsulated" by the ligand bonds and are protected from being immediately bonded with the first available negative ions thus enabling free movement between and within cells of the body. Each of the minerals will be processed in an acid-base solution, resulting in products that have a high acidity value, yet not being corrosive to living tissue. A high concentration of reactive ammonia is also produced by the acid-base reaction. Complex cations and inorganic coordination complexes are formed that are able to "encapsulate" the cations in a relatively stable fashion and allow transport throughout the body.

A method for producing a mineral cation hexa-aqua complex and ionic salt composition for treating and mitigating disease while also bolstering metabolic homeostasis of healthy cells, comprising forming hexa-coordinated complexes with one or more cationic minerals by dissolving one or more ionic salts in water, wherein the composition comprises at least one cationic mineral complex encapsulated by hexa-aqua ligands. In some embodiments, amines attached to metal ions which are slowly absorbed as the ligand structure moves toward water ligands establishing a hexa-aqua complex and freeing up the amines for assimilation along with other antioxidants including hydrogen, and sulfur and nitrogen salts. In certain embodiments, other formulations may include other salts that comprise phosphorous, nitrogen, potassium, sodium, chloride, calcium, and/or bicarbonate in combination with other metals. A prepared mixture includes at least one organic mineral complex encapsulated by hexa-aqua ligands. In some embodiments, the one or more cationic minerals comprise chromium, cobalt, copper, gold, iron, manganese, magnesium, molybdenum, nickel, platinum, silver, vanadium, and zinc. In some embodiments, the one or more ionic salts comprise nitrogen, phosphorous, potassium, sulfur, and hydrogen. In certain embodiments, a diluted mixture may be combined with a pharmaceutically acceptable carrier for delivery with other ingredients.

In some embodiments, preparing the composition includes generating a solution of ammonium hydrogen sulfate using sulfuric acid (without pH buffering), diluting the ammonia hydrogen sulfate with water to form a mixture; adding specific minerals from the designated selection to the mixture in a salt form; and agitating the mixture comprising the ammonium hydrogen sulfate, sulfuric acid, water, and the mineral salt ingredients. In certain embodiments, other salts may be incorporated in the beginning formulation, or other formulations, with other minerals utilizing the basic concept as described above with substitution of the salt preparation.

In some embodiments, generating a solution of ammonium hydrogen sulfate comprises in the following order, a) mixing ammonium sulfate with distilled water; and b) mixing sulfuric acid with the mixture comprising ammonium sulfate and distilled water, wherein the components of said mixture are added at a rate that does not result in an exothermic reaction in excess of 300° C. during either a) or b).

In some embodiments, the concentration of ammonium sulfate used in generating the solution of ammonium hydrogen sulfate is about 20% w/v or less. In some embodiments, the concentration of ammonium sulfate used in generating the solution of ammonium hydrogen sulfate is about 1%, 2%, 3%, 4%, 5%, 6%, 7%, 8%, 9%, 10%, 11%, 12%, 13%, 14%, 15%, 16%, 17%, 18%, 19%, or 20% w/v. In some embodiments, the concentration of ammonium sulfate used in generating the solution of ammonium hydrogen sulfate is between about 1% w/v and about 20% w/v. In some embodiments, the concentration of ammonium sulfate used in generating the solution of ammonium hydrogen sulfate is between about 1% w/v and 5% w/v. In some embodiments, the concentration of ammonium sulfate used in generating the solution of ammonium hydrogen sulfate is between about 5% w/v and 10% w/v. In some embodiments, the concentration of ammonium sulfate used in generating the solution of ammonium hydrogen sulfate is between about 15% w/v and 20% w/v. In some embodiments, the concentration of ammonium sulfate used in generating the solution of ammonium hydrogen sulfate is greater than about 20% w/v.

In some embodiments, the ammonium sulfate used in generating the solution of ammonium hydrogen sulfate is mixed with distilled water at a ratio between about 9:1 and about 1:15, between about 5:1 and about 1:10, between about 3:1 and about 1:5, including all ratios in between, e.g., about 3:1, about 3:2, about 2:1, about 1:2, about 1:3, about 1:4, about 1:5, about 1:6, about 1:7, about 1:8, about 1:9, about 1:10, ammonium sulfate to distilled water. In some embodiments, the ammonium sulfate used in generating the solution of ammonium hydrogen sulfate is mixed with distilled water at a ratio of 3:2 or less, ammonium sulfate to distilled water. In some embodiments, the ammonium sulfate used in generating the solution of ammonium hydrogen sulfate is mixed with distilled water at a ratio of 1:1 or less, ammonium sulfate to distilled water.

In some embodiments, the concentration of sulfuric acid used in generating the solution of ammonium hydrogen sulfate is about 18 M. In some embodiments, the sulfuric acid used in generating the solution of ammonium hydrogen sulfate is mixed with the mixture comprising ammonium sulfate and distilled water at a ratio between about 9:1 and about 1:15, between about 5:1 and about 1:10, between about 3:1 and about 1:5, including all ratios in between, e.g., about 3:1, about 3:2, about 2:1, about 1:2, about 1:3, about 1:4, about 1:5, about 1:6, about 1:7, about 1:8, about 1:9, about 1:10, sulfuric acid to mixture comprising ammonium sulfate and distilled water. In some embodiments, the sulfuric acid used in generating the solution of ammonium hydrogen sulfate is mixed with the mixture comprising ammonium sulfate and distilled water at a ratio of 1:1 or more, sulfuric acid to mixture comprising ammonium sulfate and distilled water. In some embodiments, the sulfuric acid used in generating the solution of ammonium hydrogen sulfate is mixed with the mixture comprising ammonium sulfate and distilled water at a ratio of 2:1 or less, sulfuric acid to mixture comprising ammonium sulfate and distilled water.

In some embodiments the mixture comprising ammonium sulfate, distilled water, and sulfuric acid is cooled to a temperature between about 5° C. and about 70° C. prior to adding one or more cationic minerals. In some embodiments the mixture comprising ammonium sulfate, distilled water, and sulfuric acid is cooled to a temperature between about 10° C. and about 70° C. prior to adding one or more cationic minerals. In some embodiments the mixture comprising ammonium sulfate, distilled water, and sulfuric acid is cooled to a temperature between about 20° C. and about 70° C. prior to adding one or more cationic minerals. In some embodiments the mixture comprising ammonium sulfate, distilled water, and sulfuric acid is cooled to a temperature between about 30° C. and about 70° C. prior to adding one or more cationic minerals. In some embodiments the mixture comprising ammonium sulfate, distilled water, and sulfuric acid is cooled to a temperature between about 40° C. and about 70° C. prior to adding one or more cationic minerals. In some embodiments the mixture comprising ammonium sulfate, distilled water, and sulfuric acid is cooled to a temperature between about 50° C. and about 70° C. prior to adding one or more cationic minerals. In some embodiments the mixture comprising ammonium sulfate, distilled water, and sulfuric acid is cooled to a temperature between about 60° C. and about 70° C. prior to adding one or more cationic minerals. In some embodiments the mixture comprising ammonium sulfate, distilled water, and sulfuric acid is cooled to a temperature of less than about 70° C. prior to adding one or more cationic minerals. In some embodiments the mixture comprising ammonium sulfate, distilled water, and sulfuric acid is cooled to a temperature of less than about 65.5° C. prior to adding one or more cationic minerals. In some embodiments the mixture comprising ammonium sulfate, distilled water, and sulfuric acid is cooled to a temperature of less than 65.5° C. prior to adding one or more cationic minerals. In some embodiments the mixture comprising ammonium sulfate, distilled water, and sulfuric acid is cooled to a temperature of less than 60° C. prior to adding one or more cationic minerals. In some embodiments the mixture comprising ammonium sulfate, distilled water, and sulfuric acid is cooled to a temperature of less than 50° C. prior to adding one or more cationic minerals. In some embodiments the mixture comprising ammonium sulfate, distilled water, and sulfuric acid is cooled to a temperature of about 5° C., 10° C., 20° C., 30° C., 40° C., 50° C., 60° C., or 70° C. prior to adding one or more cationic minerals.

In some embodiments, the one or more cationic minerals are added to the mixture so that the ratio of minerals is optimized for bioavailability and avoidance of adverse mineral interactions of a biological system. In some embodiments, the one or more cationic minerals are added to the mixture of ammonium sulfate, distilled water, and sulfuric acid at ratio between about 9:1 and about 1:15, between about 5:1 and about 1:10, between about 3:1 and about 1:5, including all ratios in between, e.g., about 3:1, about 3:2, about 2:1, about 1:1, about 1:2, about 1:3, about 1:4, about 1:5, about 1:6, about 1:7, about 1:8, about 1:9, about 1:10, of any of the one or more cationic minerals to one and other. In some embodiments, the one or more cationic minerals are added to the mixture of ammonium sulfate, distilled water, and sulfuric acid at ratio of at least 1:1:1, wherein the one or more cationic minerals are zinc, copper, and magnesium. In some embodiments, the one or more cationic minerals are added to the mixture of ammonium sulfate, distilled water, and sulfuric acid at a ratio of no more than 3:1:1, wherein the one or more cationic minerals are zinc, copper, and magnesium.

In some embodiments, the one or more cationic minerals are added to the mixture with one or more stabilizing materials. In some embodiments, the one or more cationic minerals are added to the mixture without one or more stabilizing materials. As used herein, a "stabilizing material" is any substance that may be used to preserve chemical and/or physical properties of a material to prevent degradation or unintended interaction. Stabilizing materials may operate inversely to that of a catalyst. Representative examples of stabilizing materials include, but are not limited to, antioxidants, sequestrants, ultraviolet stabilizers, emulsifiers, surfactants, thickeners and gelling agents, humectants, anticaking agents, coating agents, corrosion inhibitors, and inert elements.

In some embodiments of the method of producing the composition of the disclosure, the method further comprises combining the composition with a pharmaceutically acceptable carrier.

In some embodiments of the method of producing the composition of the disclosure, the method further comprises combining the composition with one or more botanical agent(s). In some embodiments, the one or more biological agent(s) comprises Graviola (*Annona muricate*), Bitter Melon (*Momordica charantia*), Esplanheira Santa (*Maytenus illcifolia*), Mullaca (*Physolis angulate*), Vasourinho (*Scoparia dulcis*), Mutamba (*Guazuma ulmifola*), Suma (*Pfaffia paniculata*), Cat's Claw (*Uncaria tomantosa*) and Blood Root (*Sanguinaria canadensis*).

Composition Permutations

A composition for treating and mitigating diseases, while also bolstering cellular metabolic functionality includes a therapeutically effective amount of a mineral cation hexa-aqua complex and ionic salt in a pharmaceutically acceptable carrier (the mineral cation hexa-aqua complex and ionic salt composition). The cationic mineral, or minerals, are bound in a hexa-aqua complex enabling transport of said ionic mineral through a biological system to a target cell.

In certain embodiments, the mineral cation of the mineral cation hexa-aqua complex and ionic salt composition may be at least one of, or any combination of, actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be actinium, and at least one of bohrium, cadmium, chromium, cobalt, copernicium, copper, darmstadtium, dubnium, gold, hafnium, hassium, iridium, iron, lanthanum, manganese, mercury, molybdenum, nickel, niobium, osmium palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be bohrium, and at least one of actinium cadmium, chromium, cobalt, copernicium, copper, darmstadtium, dubnium, gold, hafnium, hassium, iridium, iron, lanthanum, manganese, mercury, molybdenum, nickel, niobium, osmium palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be cadmium, and at least one of actinium, bohrium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be chromium, and at least one of actinium, bohrium, cadmium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be cobalt, and at least one of actinium, bohrium, cadmium, chromium, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be copernicium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be copper, and at least one of actinium, bohrium, cadmium, chromium, cobalt, copernicium, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be darmstadtium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be dubnium, and at least one of actinium, bohrium, cadmium, chromium, cobalt, copernicium, copper, darmstadtium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be gold, and at least one of actinium, bohrium, cadmium, chromium, cobalt, copernicium, copper, darmstadtium, dubnium, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be hafnium, and at least one of actinium, bohrium, cadmium, chromium, cobalt, copernicium, copper, darmstadtium, dubnium, gold, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be hassium, and at least on of actinium, bohrium, cadmium, chromium, cobalt, copernicium, copper, darmstadtium, dubnium, gold, hafnium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be iridium, and at least one of actinium, bohrium, cadmium, chromium, cobalt, copernicium, copper, darmstadtium, dubnium, gold, hafnium, hassium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be iron, and at least one of actinium, bohrium, cadmium, chromium, cobalt, copernicium, copper, darmstadtium, dubnium, gold, hafnium, hassium, iridium, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be lanthanum, and at least one of actinium, bohrium, cadmium, chromium, cobalt, copernicium, copper, darmstadtium, dubnium, gold, hafnium, hassium, iridium, iron, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be is manganese, and at least one of actinium, bohrium, cadmium, chromium, cobalt, copernicium, copper, darmstadtium, dubnium, gold, hafnium, hassium, iridium, iron, lanthanum, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be mercury, and at least one of actinium, bohrium, cadmium, chromium, cobalt, copernicium, copper, darmstadtium, dubnium, gold, hafnium, hassium, iridium, iron, lanthanum, manganese, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be molybdenum, and at least one of actinium, bohrium, cadmium, chromium, cobalt, copernicium, copper, darmstadtium, dubnium, gold, hafnium, hassium, iridium, iron, lanthanum, manganese, mercury, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be nickel, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be niobium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, osmium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be osmium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, palladium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be palladium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, platinum, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be platinum, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, rhenium, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be rhenium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhodium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be rhodium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, roentgenium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be roentgenium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, ruthenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be ruthenium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, rutherfordium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be rutherfordium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, scandium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be scandium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, seaborgium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be seaborgium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, silver, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be silver, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, tantalum, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be tantalum, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, technetium, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be technetium, and any one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, titanium, tungsten, vanadium, yttrium, zinc, or zirconium and all other forms of these minerals that are able to form metal aquo complexes. In another embodiment, the mineral cation of the mineral cation hexa-aqua complex and ionic salt composition may be titanium and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, tungsten, vanadium, yttrium, zinc, or zirconium and all other forms of these minerals that are able to form metal aquo complexes. In another embodiment, the mineral cation of the mineral cation hexa-aqua complex and ionic salt composition may be tungsten, and at least on of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, vanadium, yttrium, zinc, or zirconium and all other forms of these minerals that are able to form metal aquo complexes. In another embodiment, the mineral cation of the mineral cation hexa-aqua complex and ionic salt composition may be vanadium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, yttrium, zinc, or zirconium and all other forms of these minerals that are able to form metal aquo complexes. In another embodiment, the mineral cation of the mineral cation hexa-aqua complex and ionic salt composition may be yttrium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, zinc, or zirconium and all other forms of these minerals that are able to form metal aquo complexes. In another embodiment, the mineral cation of the mineral cation-aqua complex and ionic salt composition may be zinc, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, or zirconium and all other forms of these minerals that are able to form metal aquo complexes. In another embodiment, the cat mineral cation of the mineral cation hexa-aqua complex and ionic salt composition may be zirconium, and at least one of actinium, bohrium, cadmium, chromium, cobalt, copernicium, copper, darmstadtium, dubnium, gold, hafnium, hassium, iridium, iron, lanthanum, manganese, mercury, molybdenum, nickel, niobium, osmium, palladium, platinum, rhenium, rhodium, roentgenium, ruthenium, rutherfordium, scandium, seaborgium, silver, tantalum, technetium, titanium, tungsten, vanadium, yttrium, or zinc and all other forms of these minerals that are able to form metal aquo complexes.

In another embodiment, the mineral cation of the mineral cation hexa-aqua complex and ionic salt composition may be at least one of, or any combination of, actinium, cadmium, chromium, cobalt, copper, gold, hafnium, iridium, iron, lanthanum, manganese, mercury, molybdenum, nickel, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be actinium, and at least one of cadmium, chromium, cobalt, copper, gold, hafnium, iridium, iron, lanthanum, manganese, mercury, molybdenum, nickel, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be cadmium, and at least one of actinium, chromium, cobalt, copper, gold, hafnium, iridium, iron, lanthanum, manganese, mercury, molybdenum, nickel, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be chromium, and at least one of actinium, cadmium, cobalt, copper, gold, hafnium, iridium, iron, lanthanum, manganese, mercury, molybdenum, nickel, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be cobalt, and at least one of actinium, cadmium, chromium, copper, gold, hafnium, iridium, iron, lanthanum, manganese, mercury, molybdenum, nickel, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be copper, and at least one of actinium, cadmium, chromium, cobalt, gold, hafnium, iridium, iron, lanthanum, manganese, mercury, molybdenum, nickel, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be gold, and at least one of actinium, cadmium, chromium, cobalt, copper, hafnium, iridium, iron, lanthanum, manganese, mercury, molybdenum, nickel, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be hafnium, and at least one of actinium, cadmium, chromium, cobalt, copper, gold, iridium, iron, lanthanum, manganese, mercury, molybdenum, nickel, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be iridium, and at least one of actinium, cadmium, chromium, cobalt, copper, gold, hafnium, iron, lanthanum, manganese, mercury, molybdenum, nickel, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be iron, and at least one of actinium, cadmium, chromium, cobalt, copper, gold, hafnium, iridium, lanthanum, manganese, mercury, molybdenum, nickel, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be lanthanum, and at least one of actinium, cadmium, chromium, cobalt, copper, gold, hafnium, iridium, iron, manganese, mercury, molybdenum, nickel, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be manganese, and at least one of actinium, cadmium, chromium, cobalt, copper, gold, hafnium, iridium, iron, lanthanum, mercury, molybdenum, nickel, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be mercury, and at least one of actinium, cadmium, chromium, cobalt, copper, gold, hafnium, iridium, iron, lanthanum, manganese, molybdenum, nickel, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be molybdenum, and at least one of actinium, cadmium, chromium, cobalt, copper, gold, hafnium, iridium, iron, lanthanum, manganese, mercury, nickel, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be nickel, and at least one of actinium, cadmium, chromium, cobalt, copper, gold, hafnium, iridium, iron, lanthanum, manganese, mercury, molybdenum, niobium, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be niobium, and at least one of actinium, cadmium, chromium, cobalt, copper, gold, hafnium, iridium, iron, lanthanum, manganese, mercury, molybdenum, nickel, osmium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be osmium, and at least one of actinium, cadmium, chromium, cobalt, copper, gold, hafnium, iridium, iron, lanthanum, manganese, mercury, molybdenum, nickel, niobium, palladium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be palladium, and at least one of actinium, cadmium, chromium, cobalt, copper, gold, hafnium, iridium, iron, lanthanum, manganese, mercury, molybdenum, nickel, niobium, osmium, platinum, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be platinum, and at least one of actinium, cadmium, chromium, cobalt, copper, gold, hafnium, iridium, iron, lanthanum, manganese, mercury, molybdenum, nickel, niobium, osmium, palladium, rhenium, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be rhenium, and at least one of actinium, cadmium, chromium, cobalt, copper, gold, hafnium, iridium, iron, lanthanum, manganese, mercury, molybdenum, nickel, niobium, osmium, palladium, platinum, rhodium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be rhodium, and at least one of actinium, cadmium, chromium, cobalt, copper, gold, hafnium, iridium, iron, lanthanum, manganese, mercury, molybdenum, nickel, niobium, osmium, palladium, platinum, rhenium, ruthenium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be ruthenium, and at least one of actinium, cadmium, chromium, cobalt, copper, gold, hafnium, iridium, iron, lanthanum, manganese, mercury, molybdenum, nickel, niobium, osmium, palladium, platinum, rhenium, rhodium, scandium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be scandium, and at least one of actinium, cadmium, chromium, cobalt, copper, gold, hafnium, iridium, iron, lanthanum, manganese, mercury, molybdenum, nickel, niobium, osmium, palladium, platinum, rhenium, rhodium, ruthenium, seaborgium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be seaborgium, and at least one of actinium, cadmium, chromium, cobalt, copper, gold, hafnium, iridium, iron, lanthanum, manganese, mercury, molybdenum, nickel, niobium, osmium, palladium, platinum, rhenium, rhodium, ruthenium, scandium, silver, tantalum, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be silver, and at least one of actinium, cadmium, chromium, cobalt, copper, gold, hafnium, iridium, iron, lanthanum, manganese, mercury, molybdenum, nickel, niobium, osmium, palladium, platinum, rhenium, rhodium, ruthenium, scandium, seaborgium, tantalum, technetium, titanium, tungsten, vanadium, yttrium, zinc, or zirconium and all other forms of these minerals that are able to form hexa-aqua complexes. In another embodiment, the mineral cation of the mineral cation and ionic salt composition may be tantalum, and at least one of actinium, cadmium, chromium, cobalt, copper, gold, hafnium, iridium, iron, lanthanum, manganese, mercury, molybdenum, nickel, niobium, osmium, palladium, platinum, rhenium, rhodium, ruthenium, scandium, seaborgium, silver, technetium, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be technetium, and at least one of actinium, cadmium, chromium, cobalt, copper, gold, hafnium, iridium, iron, lanthanum, manganese, mercury, molybdenum, nickel, niobium, osmium, palladium, platinum, rhenium, rhodium, ruthenium, scandium, seaborgium, silver, tantalum, titanium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be titanium, and at least one of actinium, cadmium, chromium, cobalt, copper, gold, hafnium, iridium, iron, lanthanum, manganese, mercury, molybdenum, nickel, niobium, osmium, palladium, platinum, rhenium, rhodium, ruthenium, scandium, seaborgium, silver, tantalum, technetium, tungsten, vanadium, yttrium, zinc, or zirconium and all other forms of these minerals that are able to form hexa-aqua complexes. In another embodiment, the mineral cation of the mineral cation hexa-aqua complex and ionic salt composition may be tungsten, and at least one of actinium, cadmium, chromium, cobalt, copper, gold, hafnium, iridium, iron, lanthanum, manganese, mercury, molybdenum, nickel, niobium, osmium, palladium, platinum, rhenium, rhodium, ruthenium, scandium, seaborgium, silver, tantalum, technetium, titanium, vanadium, yttrium, zinc, or zirconium and all other forms of these minerals that are able to form hexa-aqua complexes. In another embodiment, the mineral cation of the mineral cation hexa-aqua complex and ionic salt composition may be vanadium, and at least one of actinium, cadmium, chromium, cobalt, copper, gold, hafnium, iridium, iron, lanthanum, manganese, mercury, molybdenum, nickel, niobium, osmium, palladium, platinum, rhenium, rhodium, ruthenium, scandium, seaborgium, silver, tantalum, technetium, titanium, tungsten, yttrium, zinc, or zirconium and all other forms of these minerals that are able to form hexa-aqua complexes. In another embodiment, the mineral cation of the mineral cation hexa-aqua complex and ionic salt composition may be yttrium, and at least one of actinium, cadmium, chromium, cobalt, copper, gold, hafnium, iridium, iron, lanthanum, manganese, mercury, molybdenum, nickel, niobium, osmium, palladium, platinum, rhenium, rhodium, ruthenium, scandium, seaborgium, silver, tantalum, technetium, titanium, tungsten, vanadium, zinc, or zirconium and all other forms of these minerals that are able to form hexa-aqua complexes. In another embodiment, the mineral cation of the mineral cation hexa-aqua complex and ionic salt composition may be zinc, and at least one of actinium, cadmium, chromium, cobalt, copper, gold, hafnium, iridium, iron, lanthanum, manganese, mercury, molybdenum, nickel, niobium, osmium, palladium, platinum, rhenium, rhodium, ruthenium, scandium, seaborgium, silver, tantalum, technetium, titanium, tungsten, vanadium, yttrium, or zirconium and all other forms of these minerals that are able to form hexa-aqua complexes. In another embodiment, the mineral cation of the mineral cation hexa-aqua complex and ionic salt composition may be zirconium, and at least one of actinium, cadmium, chromium, cobalt, copper, gold, hafnium, iridium, iron, lanthanum, manganese, mercury, molybdenum, nickel, niobium, osmium, palladium, platinum, rhenium, rhodium, ruthenium, scandium, seaborgium, silver, tantalum, technetium, titanium, tungsten, vanadium, yttrium, or zinc and all other forms of these minerals that are able to form hexa-aqua complexes.

In another embodiment, the mineral cation of the mineral cation hexa-aqua complex and ionic salt composition may be at least one of, or any combination of, chromium, cobalt, copper, gold, iron, manganese, magnesium, molybdenum, nickel, platinum, silver, vanadium, or zinc and all other forms of these minerals that are able to form hexa-aqua complexes. In another embodiment, the mineral cation of the mineral cation hexa-aqua complex and ionic salt composition may be chromium, and at least one of cobalt, copper, gold, iron, manganese, magnesium, molybdenum, nickel, platinum, silver, vanadium, or zinc and all other forms of these minerals that are able to form hexa-aqua complexes. In another embodiment, the mineral cation of the mineral cation hexa-aqua complex and ionic salt composition may be cobalt, and at least one of chromium, copper, gold, iron, manganese, magnesium, molybdenum, nickel, platinum, silver, vanadium, or zinc and all other forms of these minerals that are able to form hexa-aqua complexes. In another embodiment, the mineral cation of the mineral cation hexa-aqua complex and ionic salt composition may be copper, and at least one of chromium, cobalt, gold, iron, manganese, magnesium, molybdenum, nickel, platinum, silver, vanadium, or zinc and all other forms of these minerals that are able to form hexa-aqua complexes. In another embodiment, the mineral cation of the mineral cation hexa-aqua complex and ionic salt composition may be gold, and at least one of chromium, cobalt, copper, iron, manganese, magnesium, molybdenum, nickel, platinum, silver, vanadium, or zinc and all other forms of these minerals that are able to form hexa-aqua complexes. In another embodiment, the mineral cation of the mineral cation hexa-aqua complex and ionic salt composition may be iron, and at least one of chromium, cobalt, copper, gold, manganese, magnesium, molybdenum, nickel, platinum, silver, vanadium, or zinc and all other forms of these minerals that are able to form hexa-aqua complexes. In another embodiment, the mineral cation of the mineral cation hexa-aqua complex and ionic salt composition may be manganese, and any one of chromium, cobalt, copper, gold, iron, magnesium, molybdenum, nickel, platinum, silver, vanadium, or zinc and all other forms of these minerals that are able to form hexa-aqua complexes. In another embodiment, the mineral cation of the mineral cation hexa-aqua complex and ionic salt composition may be magnesium, and at least one of chromium, cobalt, copper, gold, iron, manganese, molybdenum, nickel, platinum, silver, vanadium, or zinc and all other forms of these minerals that are able to form hexa-aqua complexes. In another embodiment, the mineral cation of the mineral cation hexa-aqua complex and ionic salt composition may be molybdenum, and at least one of chromium, cobalt, copper, gold, iron, manganese, magnesium, nickel, platinum, silver, vanadium, or zinc and all other forms of these minerals that are able to form hexa-aqua complexes. In another embodiment, the mineral cation of the mineral cation hexa-aqua complex and ionic salt composition may be nickel, and at least one of chromium, cobalt, copper, gold, iron, manganese, magnesium, molybdenum, platinum, silver, vanadium, or zinc and all other forms of these minerals that are able to form hexa-aqua complexes. In another embodiment, the mineral cation of the mineral cation hexa-aqua complex and ionic salt composition may be platinum, and at least one of chromium, cobalt, copper, gold, iron, manganese, magnesium, molybdenum, silver, vanadium, or zinc and all other forms of these minerals that are able to form hexa-aqua complexes. In another embodiment, the mineral cation of the mineral cation hexa-aqua complex and ionic salt composition may be silver, and at least one of chromium, cobalt, copper, gold, iron, manganese, magnesium, molybdenum, nickel, platinum, vanadium, or zinc and all other forms of these minerals that are able to form hexa-aqua complexes. In another embodiment, the mineral cation of the mineral cation hexa-aqua complex and ionic salt composition may be vanadium, and at least one of chromium, cobalt, copper, gold, iron, manganese, magnesium, molybdenum, nickel, platinum, silver, or zinc and all other forms of these minerals that are able to form hexa-aqua complexes. In another embodiment, the mineral cation of the mineral cation hexa-aqua complex and ionic salt composition may be zinc, and at least one of chromium, cobalt, copper, gold, iron, manganese, magnesium, molybdenum, nickel, platinum, silver, or vanadium and all other forms of these minerals that are able to form hexa-aqua complexes.

In certain embodiments, the mineral cation of the mineral cation hexa-aqua complex and ionic salt composition may be copper, zinc, and magnesium.

The composition containing the mineral cation hexa-aqua complex is accompanied by an ionic salt in a pharmaceutically acceptable carrier. The composition allows the ionic salt to transport through a biological system to a target cell.

In certain embodiments, the ionic salt the of the mineral cation hexa-aqua complex and ionic salt composition may be at least one of, or any combination of, bicarbonate, calcium, chloride, sodium, sulfur, nitrogen, phosphorous, or potassium. In another embodiment, the ionic salt the of the mineral cation hexa-aqua complex and ionic salt composition may be bicarbonate, and at least one of calcium, chloride, sodium, sulfur, nitrogen, phosphorous, and potassium. In another embodiment, the ionic salt the of the mineral cation hexa-aqua complex and ionic salt composition may be calcium, and at least one of bicarbonate, chloride, sodium, sulfur, nitrogen, phosphorous, or potassium. In another embodiment, the ionic salt the of the mineral cation hexa-aqua complex and ionic salt composition may be chloride, and at least one of bicarbonate, calcium, sodium, sulfur, nitrogen, phosphorous, or potassium. In another embodiment, the ionic salt the of the mineral cation hexa-aqua complex and ionic salt composition may be sodium, and at least one of bicarbonate, calcium, chloride, sodium, sulfur, nitrogen, phosphorous, or potassium. In another embodiment the ionic salt of the mineral cation hexa-aqua complex and ionic salt composition may be sodium, and at least one of bicarbonate, calcium, chloride, sulfur, nitrogen, phosphorous, or potassium. In another embodiment, the ionic salt the of the mineral cation hexa-aqua complex and ionic salt composition may be sulfur, and at least one of bicarbonate, calcium, chloride, sodium, nitrogen, phosphorous, or potassium. In another embodiment, the ionic salt the of the mineral cation hexa-aqua complex and ionic salt composition may be nitrogen, and at least one of bicarbonate, calcium, chloride, sodium, sulfur, phosphorous, or potassium. In another embodiment, the ionic salt of the mineral cation hexa-aqua complex and ionic salt composition may be phosphorus, and at least one of bicarbonate, calcium, chloride, sodium, sulfur, nitrogen, or potassium. In another embodiment, the ionic salt the of the mineral cation hexa-aqua complex and ionic salt composition may be potassium, and at least one of bicarbonate, calcium, chloride, sodium, sulfur, nitrogen, or phosphorous.

In certain embodiments, the ionic salt of the mineral cation hexa-aqua complex and ionic salt composition may be ammonium, and hydrogen sulfate.

In certain embodiments, the mineral cation hexa-aqua complex and ionic salt composition may contain trace amounts of hydrogen cations. In another embodiment, the mineral cation hexa-aqua complex and ionic salt composition may contain about 0.01% to about 0.25% w/w.

In certain embodiments, the mineral cation hexa-aqua complex and ionic salt composition may comprise about 1% to about 5% cationic mineral hexaaqua complexes, about 1% to about 15% ionic salts, and about 80/6-98% carrier. In another embodiment, the mineral cation hexa-aqua complex and ionic salt composition may comprise about 5% to about 10% cationic mineral hexaaqua complexes, about 15% to about 25% ionic salts, and about 65% to about 80% carrier. In another embodiment, the mineral cation hexa-aqua complex and ionic salt composition may comprise about 10% to about 20% cationic mineral hexaaqua complexes, about 25% to about 50% ionic salts, and about 30% to about 65% carrier. In another embodiment, the mineral cation hexa-aqua complex and ionic salt composition may comprise about 20% to about 30% cationic mineral hexaaqua complexes, about 50% to about 70% ionic salts, and about 0%-30% carrier.

In certain embodiments, the mineral cation hexa-aqua complex and ionic salt composition may comprise hexaaquacopper (II) ion, hexaaquazinc (II) ion, hexaaquamagnesium (II) ion, hydrogen cation, ammonium, hydrogen sulfate, and water. In certain embodiments, the mineral cation hexa-aqua complex and ionic salt composition may comprise hexaaquacopper (II) ion, hexaaquazinc (II) ion, hexaaquamagnesium (II) ion, hydrogen cation, ammonium, hydrogen sulfate, and water, wherein the hexaaquacopper (II) ion may be about 1.0% to about 2.5% w/w, the hexaaquazinc (II) ion is about 3.5% to about 5.0% w/w, the hexaaquamagnesium (II) ion may be about 1.0% to about 2.5% w/w, the hydrogen cation may be about 0.04% to about 0.14%, the ammonium may be about 1.0% to about 2.5% w/w, the hydrogen sulfate may be about 18% to about 20% w/w and the water may be about 70.0% to about 71.5% w/w.

In certain embodiments, the mineral cation hexa-aqua complex and ionic salt composition may be diluted to avoid any complications associated with the pH of the composition.

The use of botanicals, vitamin and mineral supplements, and formulation additives may improve the performance of the mineral cation hexa-aqua complex and ionic salt composition. In some embodiments, the mineral cation hexa-aqua complex and ionic salt composition may further comprise botanical extracts and isolations. In one embodiment, the botanical extract of the mineral cation hexa-aqua complex and ionic salt composition may be at least one of, or any combination of, Graviola (*Annona muricate*), Bitter Melon (*Momordica charantia*), Esplanheira Santa (*Maytenus illcifolia*), Mullaca (*Physolis angulate*), Vasourinho (*Scoparia dulcis*), Mutamba (*Guazuma ulmifola*), Suma (*Pfaffia paniculata*), Cat's Claw (*Uncaria tomantosa*), or Blood Root (*Sanguinaria canadensis*). In another embodiment, the botanical extract of the mineral cation hexa-aqua complex and ionic salt composition may be Graviola (*Annona muricate*), and at least one of Bitter Melon (*Momordica charantia*), Esplanheira Santa (*Maytenus illcifolia*), Mullaca (*Physolis angulate*), Vasourinho (*Scoparia dulcis*), Mutamba (*Guazuma ulmifola*), Suma (*Pfaffia paniculata*), Cat's Claw (*Uncaria tomantosa*), or Blood Root (*Sanguinaria canadensis*). In another embodiment, the botanical extract of the mineral cation hexa-aqua complex and ionic salt composition may be Bitter Melon (*Momordica charantia*), and at least one of Graviola (*Annona muricate*), Esplanheira Santa (*Maytenus illcifolia*), Mullaca (*Physolis angulate*), Vasourinho (*Scoparia dulcis*), Mutamba (*Guazuma ulmifola*), Suma (*Pfaffia paniculata*), Cat's Claw (*Uncaria tomantosa*), or Blood Root (*Sanguinaria canadensis*). In another embodiment, the botanical extract of the mineral cation hexa-aqua complex and ionic salt composition may be Esplanheira Santa (*Maytenus illcifolia*), and at least one of Graviola (*Annona muricate*), Bitter Melon (*Momordica charantia*), Mullaca (*Physolis angulate*), Vasourinho (*Scoparia dulcis*), Mutamba (*Guazuma ulmifola*), Suma (*Pfaffia paniculata*), Cat's Claw (*Uncaria tomantosa*), or Blood Root (*Sanguinaria canadensis*). In another embodiment, the botanical extract of the mineral cation hexa-aqua complex and ionic salt composition may be Mullaca (*Physolis angulate*), and at least one of Graviola (*Annona muricate*), Bitter Melon (*Momordica charantia*), Esplanheira Santa (*Maytenus illcifolia*), Vasourinho (*Scoparia dulcis*), Mutamba (*Guazuma ulmifola*), Suma (*Pfaffia paniculata*), Cat's Claw (*Uncaria tomantosa*), or Blood Root (*Sanguinaria canadensis*). In another embodiment, the botanical extract of the mineral cation hexa-aqua complex and ionic salt composition may be Vasourinho (*Uncaria tomantosa*), and at least one of Graviola (*Annona muricate*), Bitter Melon (*Momordica charantia*), Esplanheira Santa (*Maytenus illcifolia*), Mullaca (*Physolis angulate*), Mutamba (*Guazuma ulmifola*), Suma (*Pfaffia paniculata*), Cat's Claw (*Uncaria tomantosa*), or Blood Root (*Sanguinaria canadensis*). In another embodiment, the botanical extract of the mineral cation hexa-aqua complex and ionic salt composition may be Mutamba (*Guazuma ulmifola*), and at least one of Graviola (*Annona muricate*), Bitter Melon (*Momordica charantia*), Esplanheira Santa (*Maytenus illcifolia*), Mullaca (*Physolis angulate*), Vasourinho (*Scoparia dulcis*), Suma (*Pfaffia paniculata*), Cat's Claw (*Uncaria tomantosa*), or Blood Root (*Sanguinaria canadensis*). In another embodiment, the botanical extract of the mineral cation hexa-aqua complex and ionic salt composition may be Suma (*Pfaffia paniculata*), and at least one of Graviola (*Annona muricate*), Bitter Melon (*Momordica charantia*), Esplanheira Santa (*Maytenus illcifolia*), Mullaca (*Physolis angulate*), Vasourinho (*Scoparia dulcis*), Mutamba (*Guazuma ulmifola*), Cat's Claw (*Uncaria tomantosa*), or Blood Root (*Sanguinaria canadensis*). In another embodiment, the botanical extract of the mineral cation hexa-aqua complex and ionic salt composition may be Cat's Claw (*Uncaria tomantosa*), and at least one of Graviola (*Annona muricate*), Bitter Melon (*Momordica charantia*), Esplanheira Santa (*Maytenus illcifolia*), Mullaca (*Physolis angulate*), Vasourinho (*Scoparia dulcis*), Mutamba (*Guazuma ulmifola*), Suma (*Pfaffia paniculata*), or Blood Root (*Sanguinaria canadensis*). In another embodiment, the botanical extract of the mineral cation hexa-aqua complex and ionic salt composition may be Blood Root (*Sanguinaria canadensis*), and at least one of Graviola (*Annona muricate*), Bitter Melon (*Momordica charantia*), Esplanheira Santa (*Maytenus illcifolia*), Mullaca (*Physolis angulate*), Vasourinho (*Scoparia dulcis*), Mutamba (*Guazuma ulmifola*), Suma (*Pfaffia paniculata*), or Cat's Claw (*Uncaria tomantosa*).

Composition Characteristics

The mineral cation hexa-aqua complex and ionic salt composition is a unique ligand binding delivery system that moves ionic material through various tissue layers and across the semi-permeable membranes of cells throughout a subject. The ionic content delivered intracellularly exhibits numerous beneficial characteristics. The mineral cation hexa-aqua complex and ionic salt composition, at appropriate concentration and proportion, is non-toxic to healthy cells of a subject, wherein the subject is a higher organism. In certain embodiments, the redox potential of the mineral cation hexa-aqua complex and ionic salt composition may be at least 450 Mv, wherein free radicals associated with metabolic function and disease response may be managed. In certain embodiments, the antioxidant Oxygen Radical Absorbance Capacity (ORAC) of the mineral cation hexa-aqua complex and ionic salt composition may measure about 1026 pMTE, wherein free radicals associated with metabolic function and disease response may be managed. In certain embodiments, the mineral cation hexa-aqua complex and ionic salt composition may provide greater bioavailability and time of action than ingested foods and mineral supplements. In certain embodiments, the pH of the mineral cation hexa-aqua complex and ionic salt composition registers as acidic (pH<1.0). The metal ions with positive charges reside in the middle of the ligand and pulls on the oxygen molecule of water inwards exposing the hydrogen ion to the outside of the ligand of the metal-aquo complex making the ligand as a whole act similarly to that of a hydrogen atom thereby making the ligand structure appear acid, however the product does not display a high acid profile and is easy to handle in the lab and may be safe for human consumption.

Lyme Disease

Treatment for Lyme Disease traditionally includes the use of antibiotics. The use of such treatments can however conclude with patients continuing to experience disease-associated symptoms, which has resulted in concern regarding the effectiveness of such treatment methods. Antibiotics have largely shown to be effective in treating Lyme Disease, especially when administered during early stages of infection, however bacteria are known to develop and deploy survival mechanisms, such as antibiotic resistance or tolerance. *Borrelia burgdorferi*, the pathogenic bacteria that causes Lyme Disease, has been shown to responsively adapt to host ecosystems through persistence survival via dynamic changes in morphology and formation of biofilm-like aggregates, which possess degrees of antibiotic tolerance. Thus, a strategy not involving the use of antibiotics was evaluated for the treatment of Lyme Disease. More specifically, the use of a mineral cation hexa-aqua complex and ionic salt composition was assessed for its effectiveness in alleviating symptoms and treating Lyme Disease.

All treatments comprise the mineral cation hexa-aqua complex and ionic salt composition. Exemplary subjects may be seropositive for IgG antibodies for *Borrelia burgdorferi*, optionally receive antibiotic treatments, and optionally, present evidence of spirochete in saliva samples. Subjects may present at least one Lyme Disease-associated symptom. Compositions for treatment of Lyme Disease may comprise (hexaaquacopper (II) ion $(Cu(H2O)_6^{2+})$, hexaaquazzinc (II) ion $(Zn(H2O)_6^{2+})$, hexaaquamagnesium (II) ion $(Mg(H2O)_6^{2+})$, hydrogen cation $(H^+)$, ammonium $(NH^+)$, hydrogen sulfate $(HSO^{4-})$, and water$(H_2O)$), wherein the hexaaquacopper (II) ion ranged from about 1.0 to about 2.5% w/w, the hexaaquazinc (II) ion ranged from about 3.5% to about 5.0% w/w, the hexaaquamagnesium (II) ion ranged from about 1.0% to about 2.5% w/w, the hydrogen cation ranged from about 0.04% to about 0.14%, the ammonium ranged from about 1.0% to about 2.5% w/w, the hydrogen sulfate ranged from about 18% to about 20% w/w and the water ranged from about 70.0% to about 71.5% w/w. via nebulization. The course of treatment may comprise 1.0 mL of the mineral cation hexa-aqua complex and ionic salt composition daily for 60 days.

Statements Regarding Variations

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Separate embodiments of the disclosure are also intended to be encompassed wherein the terms "comprising" or "comprise(s)" or "comprised" are optionally replaced with the terms, analogous in grammar, e.g.; "consisting/consist(s)" or "consisting essentially of/consist(s) essentially of to thereby describe further embodiments that are not necessarily coextensive. For clarification, as used herein "comprising is synonymous with "having," "including," "containing," or "characterized by," and is inclusive or open-ended and does not exclude additional, unrecited elements or method steps. As used herein, "consisting of" excludes any element, step, component, or ingredient not specified in the claim element. As used herein, the term "about" refers to a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. In any embodiment discussed in the context of a numerical value used in conjunction with the term "about," it is specifically contemplated that the term about can be omitted. The disclosure illustratively described herein suitably may be practiced in the absence of any element or elements, limitation or limitations which is not specifically disclosed herein. The disclosure has been described with reference to various specific and preferred embodiments and techniques. However, it should be understood that many variations and modifications may be made while remaining within the scope of the disclosure. It will be appreciated by one of ordinary skill in the art that compositions, methods, devices, device elements, materials, optional features, procedures and techniques other than those specifically described herein can be applied to the practice of the disclosure as broadly disclosed herein without resort to undue experimentation. All art-known functional equivalents of compositions, methods, devices, device elements, materials, procedures and techniques described herein; and portions thereof, are intended to be encompassed by this disclosure. Whenever a range is disclosed, all subranges and individual values are intended to be encompassed. This disclosure is not to be limited by the embodiments disclosed, including any shown in the drawings or exemplified in the specification, which are given by way of example or illustration and not of limitation. The compositions and methods and accessory methods described herein as presently representative of preferred embodiments are exemplary and are not intended as limitations on the scope of the disclosure.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples, therefore, specifically point out the preferred embodiments of the present invention, and are not to be construed as limiting in any way the remainder of the disclosure.

The materials and methods employed in these experiments are now described.

Example 1: Nebulization of the Mineral Cation Hexa-Aqua Complex and Ionic Salt Composition for the Treatment of Lyme Disease Background Treatment for Lyme Disease traditionally includes the use of antibiotics. The use of such treatments can however conclude with patients continuing to experience disease-associated symptoms, which has resulted in concern regarding the effectiveness of such treatment methods. Antibiotics have largely shown to be effective in treating Lyme Disease, especially when administered during early stages of infection, however bacteria are known to develop and deploy survival mechanisms, such as antibiotic resistance or tolerance. *Borrelia burgdorferi*, the pathogenic bacteria that causes Lyme Disease, has been shown to responsively adapt to host ecosystems through persistence survival via dynamic changes in morphology and formation of biofilm-like aggregates, which possess degrees of antibiotic tolerance. Thus, a strategy not involving the use of antibiotics was evaluated for the treatment of Lyme Disease. More specifically, the use of a mineral cation hexa-aqua complex and ionic salt composition was assessed for its effectiveness in alleviating symptoms and treating Lyme Disease.

Methods

Assessments were recorded via testimony. All treatments using the mineral cation hexa-aqua complex and ionic salt composition were voluntarily self-administered. Subjects included individuals who were seropositive for IgG antibodies for Borrelia burgdorferi and who did not receive antibiotic treatments, as well as individuals who were seropositive for IgG antibodies for Borrelia burgdorferi and did receive antibiotic treatments yet still had evidence of spirochete in saliva samples. Each subject indicated at least one Lyme Disease-associated symptom. Subjects at the time of treatment self-administered a composition comprising (hexaaquacopper (II) ion ($Cu(H2O)_6^{2+}$), hexaaquazinc (II) ion ($Zn(H2O)_6^{2+}$), hexaaquamagnesium (II) ion ($Mg(H2O)_6^{2+}$), hydrogen cation ($H^+$), ammonium ($NH^{4+}$), hydrogen sulfate ($HSO^{4-}$), and water($H_2O$), wherein the hexaaquacopper (II) ion ranged from about 1.0 to about 2.5% w/w, the hexaaquazinc (II) ion ranged from about 3.5% to about 5.0% w/w, the hexaaquamagnesium (II) ion ranged from about 1.0% to about 2.5% w/w, the hydrogen cation ranged from about 0.04% to about 0.14%, the ammonium ranged from about 1.0% to about 2.5% w/w, the hydrogen sulfate ranged from about 18% to about 20% w/w and the water ranged from about 70.0% to about 71.5% w/w. via nebulization. The course of treatment comprised 1.0 mL of the mineral cation hexa-aqua complex and ionic salt composition daily for 60 days. Patients were then re-evaluated for Lyme disease-associated symptoms post-treatment.

Results

All of the subjects who self-administered the cationic mineral reported alleviation of at least one Lyme Disease-associated symptom. No negative reactions, side-effects, or worsening of Lyme Disease-related symptoms were reported.

General symptom as well as persistent symptoms resulting from Lyme Disease can result in noticeable loss of health-related quality of life. Prolonged treatments using antibiotics has not been well elucidated and may cause negative secondary effects. The proposed treatment method of administering the mineral cation hexa-aqua complex and ionic salt composition appeared initially successful in providing symptom alleviation.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

What is claimed:

1. A composition comprising hexaaquacopper ions in an amount of from about 1.0% to about 2.5% w/w, hexaaquazinc ions in an amount of from about 3.5% to about 5.0% w/w, hexaaquamagnesium ions in an amount of from about 1.0% to about 2.5% w/w, hydrogen cations in an amount of from about 0.04% to about 0.14% w/w, ammonium in an amount of from about 1.0% to about 2.5% w/w, hydrogen sulfate in an amount of from about 18% to about 20% w/w, and water in an amount of from about 70% to about 71.5% w/w.

2. The composition of claim 1, wherein the composition further comprises a pharmaceutically acceptable carrier.

3. The composition gf claim 1, wherein the composition further comprises one or more botanical agent(s).

4. The composition of claim 3, wherein the one or more biological agent(s) comprises Graviola (Annona muricate), Bitter Melon (Momordica charantia), Esplanheira Santa (Maytenus illcifolia), Mullaca (Physolis angulate), Vasourinho (Scoparia dulcis), Mutamba (Guazuma ulmifola), Suma (Pfaffia paniculata), Cat's Claw (Uncaria tomantosa) and Blood Root (Sanguinaria canadensis).

5. A formulation comprising the composition of claim 1, wherein the formulation is suitable for administration in a liquid form, a suspension form, a rehydrated form, a droplet form, an aerosol form, a vaporized form, a nebulized form, a semi-solid form, a solid form, a pill form, a tablet form or a capsule form.

6. The composition of claim 1, wherein the hexaaquacopper ions are hexaaquacopper (II) ions.

7. The composition of claim 1, wherein the hexaaquazinc ions are hexaaquazinc (II) ions.

8. The composition of claim 1, wherein the hexaauqamagnesium ions are hexaaquamagnesium (II) ions.

9. The composition of claim 1, wherein the hexaaquacopper ions are hexaaquacopper (II) ions, the hexaaquazinc ions are hexaaquazinc (II) ions and the hexaauqamagnesium ions are hexaaquamagnesium (II) ions.

* * * * *